(12) United States Patent
Cheng et al.

(10) Patent No.: US 7,064,196 B2
(45) Date of Patent: Jun. 20, 2006

(54) GENES ENCODING CAROTENOID COMPOUNDS

(75) Inventors: Qiong Cheng, Wilmington, DE (US); Luan Tao, Claymont, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 1 day.

(21) Appl. No.: 10/808,979

(22) Filed: Mar. 25, 2004

(65) Prior Publication Data

US 2004/0268439 A1 Dec. 30, 2004

Related U.S. Application Data

(60) Provisional application No. 60/527,083, filed on Dec. 3, 2003, provisional application No. 60/471,904, filed on May 20, 2003.

(51) Int. Cl.
*C12N 15/31* (2006.01)
*C12N 15/54* (2006.01)
*C12N 15/55* (2006.01)

(52) U.S. Cl. .................. 536/23.7; 536/23.2; 435/193; 435/195; 435/198

(58) Field of Classification Search ............... 800/278; 536/23.2, 23.7; 435/252.31, 252.35, 254.21–254.9, 435/320.1, 419, 252.3, 254.2, 254.11, 257.2
See application file for complete search history.

(56) References Cited

U.S. PATENT DOCUMENTS

| | | |
|---|---|---|
| 5,429,939 A | 7/1995 | Misawa et al. |
| 5,530,188 A | 6/1996 | Ausich et al. |
| 5,530,189 A | 6/1996 | Ausich et al. |
| 5,545,816 A | 8/1996 | Ausich et al. |
| 5,656,472 A | 8/1997 | Ausich et al. |

FOREIGN PATENT DOCUMENTS

WO    WO 02/079395 A2    10/2002

OTHER PUBLICATIONS

Armstrong GA. 1997. Ann. Rev. Microbiol. 51:629-659.*
Bosch et al. 1994. Transgenic Research. 3:304-310.*
Walden, R and Schell, J. 1990. Eur J. Biochem. 192:563-576.*
Broun et al. 1998. Science. 282:1315-1317.*
Nells and Leenheer, Microbial sources of carotenoid pigments used in foods and feeds, Appl. Bacteriol. 70: pp. 181-191, 1991.
Misawa and Shimada, Metabolic engineering for the production of carotenoids in non-carotenogenic bacteria and yeasts, J. Biotech, vol. 59:pp. 169-181, 1998.
Hauben et al., Phytogenetic Position of Phbytopathogens within the Enterobacteriaceae, Syst. Appl. Microbiol. 21(3),: pp. 384-397, Aug. 1998.
G. Armstrong, Eubacteria Show Their True Colors: Genetics of Carotyenoid Pigment biosynthesis from Microbes to Plants, J. Bact. 176: 4795-4802, 1994.
Armstrong et al., Genetics of Eubacterial Carotenoid Biosynthesis: A Colorful Tale, Annu. Rev. Microbiol. 51: pp. 629-659, 1997.
GenBank Accession No. M87280, Pantoea agglomerans, Apr. 11, 2001.
GenBank AccessionNo. D90087, Pantoea stewartil, Dec. 18, 2002.
GenBank Accession No. AY166713, Pantoea ananatis, Aug. 24, 2002.
GenBank Accession No. AB076662, Pantoea agglomerans pv. Milletiae, Dec. 26, 2001.

* cited by examiner

*Primary Examiner*—David T. Fox

(57) ABSTRACT

Genes have been isolated from strain DC260, a member of the Enterobacteriaceae family, encoding geranylgeranyl pyrophosphate (GGPP) synthetase (CrtE), phytoene synthase (CrtB), phytoene desaturase (CrtI), lycopene cyclase (CrtY), β-carotene hydroxylase (CrtZ), and zeaxanthin glucosyl transferase (CrtX) activity. The genes and their products are useful for the conversion of farnesyl pyrophosphate to carotenoids. Vectors containing those DNA segments, host cells containing the vectors and methods for producing those enzymes by recombinant DNA technology in transformed host organisms are disclosed.

1 Claim, 6 Drawing Sheets crt gene cluster in strain DC260

SEQUENCE LISTING

<160> NUMBER OF SEQ ID NOS: 20

<210> SEQ ID NO 1
<211> LENGTH: 906
<212> TYPE: DNA
<213> ORGANISM: Enterobacteriaceae strain DC260

<400> SEQUENCE: 1

```
atgaccaccc atgtcgacac cacagcacat cagacaagcg aactccttca gctgcagcaa        60
attttacagg cgcatcttga acatttactg cctgccggac agcaaagcga tcgcgtgcgt       120
gccgcgatgc gtgccggaac gctggcgcag ggcaaacgta ttcgtccttt attactgctg       180
ctggcagcgc gcgatatggg ttgcgagctg acgcaaaatg gcgttctcga tctcgcctgt       240
gcagtggaaa tggtgcacgc ggcatcgctg attctggatg acattccctc gatggataac       300
gcgcagatgc gtcgtggtcg ccctaccgtg catcgcgaat tggtgaaaa cgtggcgatt       360 ctcgccgcca tcgcgctgct tagccgcgca tttgaagtga ttgccattgc acccggtttg       420
cctgccatac ataaatctga agcgattgct gaactctccg ctgccgtcgg cctgcagggc       480
ttagtgcaag gcaattcca ggatctgcac gacggcacgc agagccgcag cccggaagcg       540
atcgccatga ccaacgaact gaaaaccagc gtgctgtttc gcgccacgct gcaaatggcg       600
gcgattgccg ctgacgcttc accgcaggtg cggcaaagac ttagcttctt cgcccaggat       660
ttgggccagg cgtttcaact gctcgacgac ctcgccgacg gttgcaaaca caccggtaaa       720
```

```
gatgtgcacc aggatcaggg caaatccacg ctggtacaga tgctcggtgc tgacggcgcg    780
gaacgtcgcc tgcgcgatca cctgcgcagc gcagatgcac accttgcctg cgcctgccat    840
cgcggcatcg ccactcgcca atatatgcac gcgctgttta atcaacagct agcgatattc    900
aactga                                                               906
```

<210> SEQ ID NO 2
<211> LENGTH: 301
<212> TYPE: PRT
<213> ORGANISM: Enterobacteriaceae strain DC260

<400> SEQUENCE: 2

```
Met Thr Thr His Val Asp Thr Thr Ala His Gln Thr Ser Glu Leu Leu
1               5                   10                  15

Gln Leu Gln Gln Ile Leu Gln Ala His Leu Glu His Leu Leu Pro Ala
            20                  25                  30

Gly Gln Gln Ser Asp Arg Val Arg Ala Ala Met Arg Ala Gly Thr Leu
        35                  40                  45

Ala Gln Gly Lys Arg Ile Arg Pro Leu Leu Leu Leu Leu Ala Ala Arg
    50                  55                  60

Asp Met Gly Cys Glu Leu Thr Gln Asn Gly Val Leu Asp Leu Ala Cys
65                  70                  75                  80

Ala Val Glu Met Val His Ala Ala Ser Leu Ile Leu Asp Asp Ile Pro
                85                  90                  95

Ser Met Asp Asn Ala Gln Met Arg Arg Gly Arg Pro Thr Val His Arg
            100                 105                 110

Glu Phe Gly Glu Asn Val Ala Ile Leu Ala Ala Ile Ala Leu Leu Ser
        115                 120                 125

Arg Ala Phe Glu Val Ile Ala Ile Ala Pro Gly Leu Pro Ala Ile His
    130                 135                 140

Lys Ser Glu Ala Ile Ala Glu Leu Ser Ala Ala Val Gly Leu Gln Gly
145                 150                 155                 160

Leu Val Gln Gly Gln Phe Gln Asp Leu His Asp Gly Thr Gln Ser Arg
                165                 170                 175

Ser Pro Glu Ala Ile Ala Met Thr Asn Glu Leu Lys Thr Ser Val Leu
            180                 185                 190

Phe Arg Ala Thr Leu Gln Met Ala Ala Ile Ala Ala Asp Ala Ser Pro
        195                 200                 205

Gln Val Arg Gln Arg Leu Ser Phe Phe Ala Gln Asp Leu Gly Gln Ala
    210                 215                 220

Phe Gln Leu Leu Asp Asp Leu Ala Asp Gly Cys Lys His Thr Gly Lys
225                 230                 235                 240

Asp Val His Gln Asp Gln Gly Lys Ser Thr Leu Val Gln Met Leu Gly
                245                 250                 255

Ala Asp Gly Ala Glu Arg Arg Leu Arg Asp His Leu Arg Ser Ala Asp
            260                 265                 270

Ala His Leu Ala Cys Ala Cys His Arg Gly Ile Ala Thr Arg Gln Tyr
        275                 280                 285

Met His Ala Leu Phe Asn Gln Gln Leu Ala Ile Phe Asn
    290                 295                 300
```

<210> SEQ ID NO 3
<211> LENGTH: 1278
<212> TYPE: DNA
<213> ORGANISM: Enterobacteriaceae strain DC260

<400> SEQUENCE: 3

```
gtgggccact ttgcggtgat cgcgccgccg ctctacagcc actttcacgc gttgcaggcg      60
ttagcacaaa cgctgctggc gcgcggccat cgcatcacat tcatccagca agccgatgcc     120
cgcactttgc ttagcgacga acgcatcgat tttgttgccg tcggccaaca gacgcatcct     180
gccggttcgc tggcgcccgt gttgcatcgg ctggcctcgc cgggcggcct gtcgctgttt     240
cgcgtgatcg acgatctcgc gtcctgcacc gatatgctgt gccgcgaact gcctgcggta     300
ctgaaagcat tgaacatcga tggcgtgatc gccgacgaaa tggaagcggc gggcggattg     360
gtcgctgaag cgctgcatct gccgtttgtt tcggtggcct gcgccttgcc ggtcaatcgt     420
gaagccggga ttccgcttgc ggtgatgccc ttccgttttg cacaggatga caaagcgctg     480
aaacgttttc aggccagcag cgatatctat gatcgcatca tgcgtcgtca cggcgacgtg     540
atcctcaaac acgcgcgggc gtttaatttg acggagcggc gcggattaca tcagtgcctg     600
tcgccgctgg cacaaatcag ccagatggtg ccggcctttg attttccacg tcagcaactg     660
cccgcctgct atcacgccgt ggggccactc cgcgccccgg tttctcctgc gccgctccat     720
gcgcccctggc cagcgctgcg tcagccggtg gtttatgcct cgctgggtac gctgcaaggc     780
catcgcttcc ggctgtttct gcatctggcg caggcgtgcc gccagctgcg gctatcgctg     840
gtgatcgccc attgtggggg attaaacgcc gaacagacgc atcagctgga gctcgctggc     900
gcggcgtggg tgacggattt cgtcgatcag cgcgcagccc tacagcacgc gcagctgttt     960
atcactcatg ccgggttaaa cagcgcgctg gaagcactgg aatgcggtac gccgatgctg    1020
gcgctgccga ttgcttttga tcagcccggc gtggcggcgc gcattgagtg gcatgacgtt    1080
ggtcgccgcg catcacgctt tagccgtgtt catcaactgg agcagcatct gcaacagctg    1140
ctgaccgacg atcgttacgc gctacggatg tcagcgattc aggcgcagct gcagcgcgca    1200
ggcggttgcc agcgtgccgc cgacatcgtc gagcaggcgc tgtgccagca gcaagtcgtg    1260
ctggcggagg cgacctga                                                  1278
```

<210> SEQ ID NO 4
<211> LENGTH: 425
<212> TYPE: PRT
<213> ORGANISM: Enterobacteriaceae strain DC260

<400> SEQUENCE: 4

```
Met Gly His Phe Ala Val Ile Ala Pro Pro Leu Tyr Ser His Phe His
1               5                   10                  15
Ala Leu Gln Ala Leu Ala Gln Thr Leu Leu Ala Arg Gly His Arg Ile
            20                  25                  30
Thr Phe Ile Gln Gln Ala Asp Ala Arg Thr Leu Leu Ser Asp Glu Arg
        35                  40                  45
Ile Asp Phe Val Ala Val Gly Gln Gln Thr His Pro Ala Gly Ser Leu
    50                  55                  60
Ala Pro Val Leu His Arg Leu Ala Ser Pro Gly Gly Leu Ser Leu Phe
65                  70                  75                  80
Arg Val Ile Asp Asp Leu Ala Ser Cys Thr Asp Met Leu Cys Arg Glu
                85                  90                  95
Leu Pro Ala Val Leu Lys Ala Leu Asn Ile Asp Gly Val Ile Ala Asp
            100                 105                 110
Glu Met Glu Ala Ala Gly Gly Leu Val Ala Glu Ala Leu His Leu Pro
        115                 120                 125
Phe Val Ser Val Ala Cys Ala Leu Pro Val Asn Arg Glu Ala Gly Ile
```

```
                  130                 135                 140
Pro Leu Ala Val Met Pro Phe Arg Phe Ala Gln Asp Asp Lys Ala Leu
145                 150                 155                 160

Lys Arg Phe Gln Ala Ser Ser Asp Ile Tyr Asp Arg Ile Met Arg Arg
                165                 170                 175

His Gly Asp Val Ile Leu Lys His Ala Arg Ala Phe Asn Leu Thr Glu
            180                 185                 190

Arg Arg Gly Leu His Gln Cys Leu Ser Pro Leu Ala Gln Ile Ser Gln
        195                 200                 205

Met Val Pro Ala Phe Asp Phe Pro Arg Gln Gln Leu Pro Ala Cys Tyr
    210                 215                 220

His Ala Val Gly Pro Leu Arg Ala Pro Val Ser Pro Ala Pro Leu His
225                 230                 235                 240

Ala Pro Trp Pro Ala Leu Arg Gln Pro Val Val Tyr Ala Ser Leu Gly
                245                 250                 255

Thr Leu Gln Gly His Arg Phe Arg Leu Phe Leu His Leu Ala Gln Ala
                260                 265                 270

Cys Arg Gln Leu Arg Leu Ser Leu Val Ile Ala His Cys Gly Gly Leu
            275                 280                 285

Asn Ala Glu Gln Thr His Gln Leu Glu Leu Ala Gly Ala Ala Trp Val
        290                 295                 300

Thr Asp Phe Val Asp Gln Arg Ala Ala Leu Gln His Ala Gln Leu Phe
305                 310                 315                 320

Ile Thr His Ala Gly Leu Asn Ser Ala Leu Glu Ala Leu Glu Cys Gly
                325                 330                 335

Thr Pro Met Leu Ala Leu Pro Ile Ala Phe Asp Gln Pro Gly Val Ala
                340                 345                 350

Ala Arg Ile Glu Trp His Asp Val Gly Arg Arg Ala Ser Arg Phe Ser
            355                 360                 365

Arg Val His Gln Leu Glu Gln His Leu Gln Gln Leu Leu Thr Asp Asp
        370                 375                 380

Arg Tyr Ala Leu Arg Met Ser Ala Ile Gln Ala Gln Leu Gln Arg Ala
385                 390                 395                 400

Gly Gly Cys Gln Arg Ala Ala Asp Ile Val Glu Gln Ala Leu Cys Gln
                405                 410                 415

Gln Gln Val Val Leu Ala Glu Ala Thr
                420                 425

<210> SEQ ID NO 5
<211> LENGTH: 1167
<212> TYPE: DNA
<213> ORGANISM: Enterobacteriaceae strain DC260

<400> SEQUENCE: 5
atgcgcacgc aatacgatgt gattttggtc ggtgctggac tggcgaatgg cttgattgcg      60
ctgcgtctgc gtcaattgca gccacaactg aaatgcctgt tgctggagag cgatgcgcat     120
ccggcaggca atcatacctg gtcgtttcat cacagcgatc tcagcgccga caacttcgc     180 tggctgcaac gctgattac cgtgcgttgg tcaggttatc aggtgcgttt tcctgcgctg     240
cgccgcaatc tggacgggga ttattgttcc atcgcatcag gcgatttgc ccgccatctt     300 tacgcggcga tgggtgacga tctgtggaca aacacagccg tacaacaggt aaaacccacg     360
caggtgacgc tggcggatgg ccgtgaactt gctgcgcaag tggtgattga tggtcgcggc     420
ctgcagccga cgccacatct gcagctgggt tatcaggtgt tcttggaca agagtggcag     480
```

```
ctggcgcagc cgcacggcct gcagcagccg atcctgatgg atgccaccgt cgatcagcaa    540
gcgggttatc gttttgtcta cacgctgccg ctcagcgccg atcggctatt gattgaagat    600
acccattacg ttaaccagcc cgcgctggcg gagaacaccg ctcgtcagca catcgccgac    660
tatgccaatc agcaaggctg gacgctgagt acgctgctgc gtgaagagca cggcatatta    720
ccgattaccc tgagcggcaa catcgatcga ttctggcaac agcagcgcgg ccaagcgtgc    780
agcggcctgc gcgccgggct gtttcatgcc accaccggtt actccttgcc gtccgccgtg    840
gcgctagcgg agttggtagc agcgctgttg cccaccgatg ccctcacgct cagccaacat    900
atcgaacgct ttgcccgtca gcagtggcgc gaacagcgat ttttccgtct gctaaaccgc    960
atgctgtttt tggccggtaa gccgcagcag cgctggcgcg tgatgcaacg tttttaccgg   1020
ctcgatgccg ggttaattag ccgctttac gccgggcaac tgcgcctgcg cgataaaacg    1080
cggattctgt gcggcaagcc gccggtgccc atcggtgaag cgctgcgcgc gctgttgaat   1140
tctgtcgaac cagggaagaa aaaatga                                       1167

<210> SEQ ID NO 6
<211> LENGTH: 388
<212> TYPE: PRT
<213> ORGANISM: Enterobacteriaceae strain DC260

<400> SEQUENCE: 6
```

Met Arg Thr Gln Tyr Asp Val Ile Leu Val Gly Ala Gly Leu Ala Asn
1               5                   10                  15

Gly Leu Ile Ala Leu Arg Leu Arg Gln Leu Gln Pro Gln Leu Lys Cys
            20                  25                  30

Leu Leu Leu Glu Ser Asp Ala His Pro Ala Gly Asn His Thr Trp Ser
        35                  40                  45

Phe His His Ser Asp Leu Ser Ala Glu Gln Leu Arg Trp Leu Gln Pro
    50                  55                  60

Leu Ile Thr Val Arg Trp Ser Gly Tyr Gln Val Arg Phe Pro Ala Leu
65                  70                  75                  80

Arg Arg Asn Leu Asp Gly Asp Tyr Cys Ser Ile Ala Ser Gly Asp Phe
                85                  90                  95

Ala Arg His Leu Tyr Ala Ala Met Gly Asp Asp Leu Trp Thr Asn Thr
            100                 105                 110

Ala Val Gln Gln Val Lys Pro Thr Gln Val Thr Leu Ala Asp Gly Arg
        115                 120                 125

Glu Leu Ala Ala Gln Val Val Ile Asp Gly Arg Gly Leu Gln Pro Thr
    130                 135                 140

Pro His Leu Gln Leu Gly Tyr Gln Val Phe Leu Gly Gln Glu Trp Gln
145                 150                 155                 160

Leu Ala Gln Pro His Gly Leu Gln Gln Pro Ile Leu Met Asp Ala Thr
                165                 170                 175

Val Asp Gln Gln Ala Gly Tyr Arg Phe Val Tyr Thr Leu Pro Leu Ser
            180                 185                 190

Ala Asp Arg Leu Leu Ile Glu Asp Thr His Tyr Val Asn Gln Pro Ala
        195                 200                 205

Leu Ala Glu Asn Thr Ala Arg Gln His Ile Ala Asp Tyr Ala Asn Gln
    210                 215                 220

Gln Gly Trp Thr Leu Ser Thr Leu Leu Arg Glu Glu His Gly Ile Leu
225                 230                 235                 240

Pro Ile Thr Leu Ser Gly Asn Ile Asp Arg Phe Trp Gln Gln Gln Arg

```
                   245                 250                 255
Gly Gln Ala Cys Ser Gly Leu Arg Ala Gly Leu Phe His Ala Thr Thr
                260                 265                 270

Gly Tyr Ser Leu Pro Ser Ala Val Ala Leu Ala Glu Leu Val Ala Ala
            275                 280                 285

Leu Leu Pro Thr Asp Ala Leu Thr Leu Ser Gln His Ile Glu Arg Phe
        290                 295                 300

Ala Arg Gln Gln Trp Arg Glu Gln Arg Phe Phe Arg Leu Leu Asn Arg
305                 310                 315                 320

Met Leu Phe Leu Ala Gly Lys Pro Gln Gln Arg Trp Arg Val Met Gln
                325                 330                 335

Arg Phe Tyr Arg Leu Asp Ala Gly Leu Ile Ser Arg Phe Tyr Ala Gly
                340                 345                 350

Gln Leu Arg Leu Arg Asp Lys Thr Arg Ile Leu Cys Gly Lys Pro Pro
            355                 360                 365

Val Pro Ile Gly Glu Ala Leu Arg Ala Leu Leu Asn Ser Val Glu Pro
        370                 375                 380

Gly Lys Lys Lys
385

<210> SEQ ID NO 7
<211> LENGTH: 1482
<212> TYPE: DNA
<213> ORGANISM: Enterobacteriaceae strain DC260

<400> SEQUENCE: 7
atgaaacgca cttatgtgat tggcgcaggc tttggcggcc tggcgctggc gattcgcctg      60
caagcggcgg gcataccaac caccttactc gagcagcgcg acaaaccggg cggacgcgcc     120
tatgtgtttg aggacagtgg cttttacctt cgatgccgga ccacggtgat caccgatccc     180
agcgccatcg aagagttgtt cacgctggca ggaaaatcgc tcagcgatta cgtcgagctg     240
atgccggtaa cgcccttcta tcgcctgtgc tgggaagatg caaacagct tgattacgac      300
aataatcagc gctgctgga gcagcagatc gccacgttca atccgcaaga gtagaaggc       360
tatcgtcaat tcttgccta ttcacgtgaa gtatttagag agggttatct gaaactcggc      420
acggtgccgt tctgcaggt gcgtgacatg ctgcgcgtcg cgccgcagtt gggacgtctg      480
caagcatggc gcagcgtcta gcatggtg gcgaaattta ttcaggacga tcatctgcgt       540
caggcgtttt cctccactc attgctggtg gcggtaatc cttttgcaac gtcatcgatc       600
tataccttaa ttcatgcgct ggagcgtgaa tggggcgtgt ggtttccgcg cggcggcacc     660
ggcgcgctgg tgcagggcat ggcgcgactg ttcgaggact gggcggcga gctgttactg      720
aatgccgaag tgagccagct ggaaaccagc ggcaatcgca ttagcggcgt tcagttagag     780
ggcggacgac gcttcgatgc cgccgctgtg gcctccaatg ccgacgtggt gcataccctac    840
gacaaactgc ttcgccacca tccgctggca atgaaacgtg cgacatcgct gaagcgtaag    900
cgcatgagca actcgctgtt tgtactctat tttggcctga atcagccgca tgaacagctc     960
gcgcaccaca ccgtctgttt tggcccgcgt tatcgtgagt tgatcgatga ttttttcaac    1020
agcagccagc tggcagacga ttttcactt tacctgcacg cgccctgcag cagcgatccg    1080
tcgctggcac cgcccggctg cggcagcttt tatgtgttag cgccggtgcc gcatctcggc    1140
accgctgaca tcgactggca acaggaagga ccgcgcttgc gcgatcgaat ttttgcttat    1200
ctggagcagc actacatgcc gggattacgt cagcaattag tgcacacag aatgtttacg     1260
```

```
ccgtttgatt ttcgcgacac gctgcatgcc catcacggct cggcgttttc gctggagccg    1320
attttgacgc aaagcgcctg gttccgcccg cataaccgcg atgccgatat cagcaatctc    1380
tatctggtgg gtgccggtac gcatccaggc gcgggcgtgc ccggcgtgat cggttcggcc    1440
aaggccaccg ccaggctgat gctggaggat cgcgccgaat ga                       1482
```

<210> SEQ ID NO 8
<211> LENGTH: 493
<212> TYPE: PRT
<213> ORGANISM: Enterobacteriaceae strain DC260

<400> SEQUENCE: 8

```
Met Lys Arg Thr Tyr Val Ile Gly Ala Gly Phe Gly Gly Leu Ala Leu
1               5                   10                  15

Ala Ile Arg Leu Gln Ala Ala Gly Ile Pro Thr Thr Leu Leu Glu Gln
            20                  25                  30

Arg Asp Lys Pro Gly Gly Arg Ala Tyr Val Phe Glu Asp Ser Gly Phe
        35                  40                  45

Thr Phe Asp Ala Gly Pro Thr Val Ile Thr Asp Pro Ser Ala Ile Glu
    50                  55                  60

Glu Leu Phe Thr Leu Ala Gly Lys Ser Leu Ser Asp Tyr Val Glu Leu
65                  70                  75                  80

Met Pro Val Thr Pro Phe Tyr Arg Leu Cys Trp Glu Asp Gly Lys Gln
                85                  90                  95

Leu Asp Tyr Asp Asn Asn Gln Pro Leu Leu Glu Gln Gln Ile Ala Thr
            100                 105                 110

Phe Asn Pro Gln Asp Val Glu Gly Tyr Arg Gln Phe Leu Ala Tyr Ser
        115                 120                 125

Arg Glu Val Phe Arg Glu Gly Tyr Leu Lys Leu Gly Thr Val Pro Phe
    130                 135                 140

Leu Gln Val Arg Asp Met Leu Arg Val Ala Pro Gln Leu Gly Arg Leu
145                 150                 155                 160

Gln Ala Trp Arg Ser Val Tyr Ser Met Val Ala Lys Phe Ile Gln Asp
                165                 170                 175

Asp His Leu Arg Gln Ala Phe Ser Phe His Ser Leu Leu Val Gly Gly
            180                 185                 190

Asn Pro Phe Ala Thr Ser Ser Ile Tyr Thr Leu Ile His Ala Leu Glu
        195                 200                 205

Arg Glu Trp Gly Val Trp Phe Pro Arg Gly Gly Thr Gly Ala Leu Val
    210                 215                 220

Gln Gly Met Ala Arg Leu Phe Glu Asp Leu Gly Gly Glu Leu Leu Leu
225                 230                 235                 240

Asn Ala Glu Val Ser Gln Leu Glu Thr Ser Gly Asn Arg Ile Ser Gly
                245                 250                 255

Val Gln Leu Glu Gly Gly Arg Arg Phe Asp Ala Ala Ala Val Ala Ser
            260                 265                 270

Asn Ala Asp Val Val His Thr Tyr Asp Lys Leu Leu Arg His His Pro
        275                 280                 285

Leu Ala Met Lys Arg Ala Thr Ser Leu Lys Arg Lys Arg Met Ser Asn
    290                 295                 300

Ser Leu Phe Val Leu Tyr Phe Gly Leu Asn Gln Pro His Glu Gln Leu
305                 310                 315                 320

Ala His His Thr Val Cys Phe Gly Pro Arg Tyr Arg Glu Leu Ile Asp
                325                 330                 335
```

```
Glu Ile Phe Asn Ser Ser Gln Leu Ala Asp Asp Phe Ser Leu Tyr Leu
                340                 345                 350

His Ala Pro Cys Ser Ser Asp Pro Ser Leu Ala Pro Pro Gly Cys Gly
            355                 360                 365

Ser Phe Tyr Val Leu Ala Pro Val Pro His Leu Gly Thr Ala Asp Ile
    370                 375                 380

Asp Trp Gln Gln Glu Gly Pro Arg Leu Arg Asp Arg Ile Phe Ala Tyr
385                 390                 395                 400

Leu Glu Gln His Tyr Met Pro Gly Leu Arg Gln Gln Leu Val Thr His
                405                 410                 415

Arg Met Phe Thr Pro Phe Asp Phe Arg Asp Thr Leu His Ala His His
            420                 425                 430

Gly Ser Ala Phe Ser Leu Glu Pro Ile Leu Thr Gln Ser Ala Trp Phe
        435                 440                 445

Arg Pro His Asn Arg Asp Ala Asp Ile Ser Asn Leu Tyr Leu Val Gly
    450                 455                 460

Ala Gly Thr His Pro Gly Ala Gly Val Pro Gly Val Ile Gly Ser Ala
465                 470                 475                 480

Lys Ala Thr Ala Arg Leu Met Leu Glu Asp Arg Ala Glu
                485                 490

<210> SEQ ID NO 9
<211> LENGTH: 930
<212> TYPE: DNA
<213> ORGANISM: Enterobacteriaceae strain DC260

<400> SEQUENCE: 9
atgaatcgac agcctttact tgagcaagta acgcaaacca tggcggtggg ctcgaagagt      60
ttcgccaccg ccgccaagct gttttgatgca ccgacgcgcc gcagcacgct gatgctgtat     120
gcgtggtgtc gtcactgcga tgatgtgatt gatgggcaaa cgctgggcga aggcggcacg     180
cagcatgccg tcgaagacgc gcaggcacgt atgcagcatc tgcaaattga acccgccgc      240 gcctacagcg cgcgcacat ggatgaaccg gcgtttaggg cgtttcagga agtggcgatc      300
attcaccagc tgccgcaaca actggcgttt gatcatctgg aaggcttcgc tatggatgca     360
cgcaacgaac attacgcgag cttcgatgac acgctgcgtt actgctatca cgtcgcgggc     420
gtggtcggtt tgatgatggc gcgcgtaatg ggcgtgcgcg acgaagcggt gctcgatcac     480
gcctgcgatt taggactggc gttccagctc actaacattg cgcgcgacat tgtagaagat     540
gccgaaaatg gtcgctgcta tctgccgcaa tcctggctcg atcaggcggg attacgcgcc     600
gatacgctga ctgcaccgca acatcgtgca gcgctcgcct cactggcagc gcgtttagtg     660
gcggaggcgg aaccctatta tcactcggcg cgatccggtt taccgggttt accgctgcgc     720
tcggcgtggg ccatcgctac ggctcgcggc gtttatcgcg aaattggcgt caaagttcag     780
cacgccggtg tgcacgcctg ggattcacgg cagcgcacca gtaaaggtga aaaactggcg     840
ctgctggtga aggggcagg tttggcgatc acttcgcgtg tgtctcgtcc tgaaccgcgt     900
ccggctggtc tgtggcagcg tcctcgttga                                     930

<210> SEQ ID NO 10
<211> LENGTH: 309
<212> TYPE: PRT
<213> ORGANISM: Enterobacteriaceae strain DC260

<400> SEQUENCE: 10

Met Asn Arg Gln Pro Leu Leu Glu Gln Val Thr Gln Thr Met Ala Val
```

|   |   |   |   |   |   |   |   |   |   |   |   |   |   |   |
|---|---|---|---|---|---|---|---|---|---|---|---|---|---|---|
| 1 |   |   |   | 5 |   |   |   |   | 10 |   |   |   |   | 15 |

Gly Ser Lys Ser Phe Ala Thr Ala Ala Lys Leu Phe Asp Ala Pro Thr
              20                  25                  30

Arg Arg Ser Thr Leu Met Leu Tyr Ala Trp Cys Arg His Cys Asp Asp
          35                  40                  45

Val Ile Asp Gly Gln Thr Leu Gly Glu Gly Gly Thr Gln His Ala Val
     50                  55                  60

Glu Asp Ala Gln Ala Arg Met Gln His Leu Gln Ile Glu Thr Arg Arg
65                  70                  75                  80

Ala Tyr Ser Gly Ala His Met Asp Glu Pro Ala Phe Arg Ala Phe Gln
             85                  90                  95

Glu Val Ala Ile Ile His Gln Leu Pro Gln Gln Leu Ala Phe Asp His
             100                 105                 110

Leu Glu Gly Phe Ala Met Asp Ala Arg Asn Glu His Tyr Ala Ser Phe
            115                 120                 125

Asp Asp Thr Leu Arg Tyr Cys Tyr His Val Ala Gly Val Val Gly Leu
        130                 135                 140

Met Met Ala Arg Val Met Gly Val Arg Asp Glu Ala Val Leu Asp His
145                 150                 155                 160

Ala Cys Asp Leu Gly Leu Ala Phe Gln Leu Thr Asn Ile Ala Arg Asp
                165                 170                 175

Ile Val Glu Asp Ala Glu Asn Gly Arg Cys Tyr Leu Pro Gln Ser Trp
            180                 185                 190

Leu Asp Gln Ala Gly Leu Arg Ala Asp Thr Leu Thr Ala Pro Gln His
        195                 200                 205

Arg Ala Ala Leu Ala Ser Leu Ala Ala Arg Leu Val Ala Glu Ala Glu
    210                 215                 220

Pro Tyr Tyr His Ser Ala Arg Ser Gly Leu Pro Gly Leu Pro Leu Arg
225                 230                 235                 240

Ser Ala Trp Ala Ile Ala Thr Ala Arg Gly Val Tyr Arg Glu Ile Gly
                245                 250                 255

Val Lys Val Gln His Ala Gly Val His Ala Trp Asp Ser Arg Gln Arg
            260                 265                 270

Thr Ser Lys Gly Glu Lys Leu Ala Leu Leu Val Lys Gly Ala Gly Leu
        275                 280                 285

Ala Ile Thr Ser Arg Val Ser Arg Pro Glu Pro Arg Pro Ala Gly Leu
    290                 295                 300

Trp Gln Arg Pro Arg
305

<210> SEQ ID NO 11
<211> LENGTH: 534
<212> TYPE: DNA
<213> ORGANISM: Enterobacteriaceae strain DC260

<400> SEQUENCE: 11
atgctctggt tatggaacgt gcttatcttg ttggcaaccg tggtggtgat ggaaatcgta      60
gcggcgctgt cgcataaata tcatcatgca cggttgggga tggggctggca tctgtcgcac     120 catgaaccgc acagcggtaa gtttgagctc aacgatcttt atgcggtggt gtttgcggta     180
ctggcgattg tgctgattta tgtcggtgtg caaggcatgt ggccgctgca gtggattggt     240
gccggaatga cgacgtacgg cgcgctctac ttcatggtgc acgatggcct ggtgcatcaa     300
cgctggccgt tccgctatat cccgcgcaaa ggctatctta agcgcttata catggcgcac     360

```
cgcatgcatc atgcggtgcg cgggcgtgaa ggctgcgtgt cgtttggttt cctctacgcg      420
ccaccgctga ataagctgca agccacgctg cgccagcgtc acggacgtaa aatcaacgag      480
gacgctgcca cagaccagcc ggacgcggtt caggacgaga cacacgcgaa gtga            534
```

```
<210> SEQ ID NO 12
<211> LENGTH: 177
<212> TYPE: PRT
<213> ORGANISM: Enterobacteriaceae strain DC260

<400> SEQUENCE: 12
```

Met Leu Trp Leu Trp Asn Val Leu Ile Leu Ala Thr Val Val
1               5                   10                  15

Met Glu Ile Val Ala Ala Leu Ser His Lys Tyr Ile Met His Gly Trp
                20                  25                  30

Gly Trp Gly Trp His Leu Ser His His Glu Pro His Ser Gly Lys Phe
            35                  40                  45

Glu Leu Asn Asp Leu Tyr Ala Val Val Phe Ala Val Leu Ala Ile Val
        50                  55                  60

Leu Ile Tyr Val Gly Val Gln Gly Met Trp Pro Leu Gln Trp Ile Gly
65                  70                  75                  80

Ala Gly Met Thr Thr Tyr Gly Ala Leu Tyr Phe Met Val His Asp Gly
                85                  90                  95

Leu Val His Gln Arg Trp Pro Phe Arg Tyr Ile Pro Arg Lys Gly Tyr
            100                 105                 110

Leu Lys Arg Leu Tyr Met Ala His Arg Met His His Ala Val Arg Gly
        115                 120                 125

Arg Glu Gly Cys Val Ser Phe Gly Phe Leu Tyr Ala Pro Pro Leu Asn
    130                 135                 140

Lys Leu Gln Ala Thr Leu Arg Gln Arg His Gly Arg Lys Ile Asn Glu
145                 150                 155                 160

Asp Ala Ala Thr Asp Gln Pro Asp Ala Val Gln Asp Glu Thr His Ala
                165                 170                 175

Lys

```
<210> SEQ ID NO 13
<211> LENGTH: 19
<212> TYPE: DNA
<213> ORGANISM: Artificial Sequence
<220> FEATURE:
<223> OTHER INFORMATION: Primer HK12

<400> SEQUENCE: 13
gagtttgatc ctggctcag                                                  19

<210> SEQ ID NO 14
<211> LENGTH: 15
<212> TYPE: DNA
<213> ORGANISM: Artificial Sequence
<220> FEATURE:
<223> OTHER INFORMATION: Primer JCR14

<400> SEQUENCE: 14
acgggcggtg tgtac                                                      15

<210> SEQ ID NO 15
<211> LENGTH: 16
<212> TYPE: DNA
<213> ORGANISM: Artificial Sequence
<220> FEATURE:
```

<223> OTHER INFORMATION: Primer JCR15

<400> SEQUENCE: 15
gccagcagcc gcggta                                                    16

<210> SEQ ID NO 16
<211> LENGTH: 1327
<212> TYPE: DNA
<213> ORGANISM: Enterobacteriaceae strain DC260

<400> SEQUENCE: 16
gaacgctggc ggcaggccta acacatgcaa gtcgaacggt agcacagaga gcttgctctc      60
gggtgacgag tggcggacgg gtgagtaatg tctgggaaac tgcccgatgg aggggataa      120 ctactggaaa cggtagctaa taccgcataa cgtcgcaaga ccaaagtggg ggaccttcgg     180
gcctcacacc atcggatgtg cccagatggg attagctagt aggtggggta atggctcacc     240
taggcgacga tccctagctg gtctgagagg atgaccagcc acactggaac tgagacacgg     300
tccagactcc tacgggaggc agcagtgggg aatattgcac aatgggcgca agcctgatgc     360
agccatgccg cgtgtatgaa gaaggccttc gggttgtaaa gtactttcag cggggaggaa     420
ggcggtgaag ttaatagctt caccgattga cgttacccgc agaagaaagc accggctaac     480
tccgtgccag cagccgcggt aatacggagg gtgcaagcgt taatcggaat tactgggcgt     540
aaaagcgcac gcaggcggtc tgtcaagtcg gatgtgaaat ccccgggctt aacctgggaa     600
ctgcattcga aactggcagg ctagagtctt gtagaggggg gtagaattcc aggtgtagcg     660
gtgaaatgcg tagagatctg gaggaatacc ggtggcgaag gcggccccct ggacaaagac     720
tgacgctcag gtgcgaaagc gtggggagca acaggatta gatacctgg tagtccacgc     780 cgtaaacgat gtcgacttgg aggttgttcc cttgaggagt ggcttccgga gctaacgcgt     840
taagtcgacc gcctggggag tacgccgca aggttaaaac tcaaatgaat tgacggggc      900 ccgcacaagc ggtggagcat gtggtttaat tcgatgcaac gcgaagaacc ttacctactc     960
ttgacatcca gagaacttag cagagatgct ttggtgcctt cgggaactct gagacaggtg    1020
ctgcatggct gtcgtcagct cgtgttgtga aatgttgggt taagtcccgc aacgagcgca    1080
acccttatcc tttgttgcca gcggttcggc cgggaactca aggagactg ccagtgataa     1140 actggaggaa ggtggggatg acgtcaagtc atcatggccc ttacgagtag ggctacacac    1200
gtgctacaat ggcgcataca aagagaagcg acctcgcgag agcaagcgga cctcataaag    1260
tgcgtcgtag tccggatcgg agtctgcaac tcgactccgt gaagtcggaa tcgctagtaa    1320
tcgtaga                                                             1327

<210> SEQ ID NO 17
<211> LENGTH: 23
<212> TYPE: DNA
<213> ORGANISM: Artificial Sequence
<220> FEATURE:
<223> OTHER INFORMATION: Primer TET-1 FP-1

<400> SEQUENCE: 17
gggtgcgcat gatcctctag agt                                            23

<210> SEQ ID NO 18
<211> LENGTH: 6999
<212> TYPE: DNA
<213> ORGANISM: Enterobacteriaceae strain DC260

<400> SEQUENCE: 18

-continued

```
gcgatggcaa tggaaaatgt tgcgtgagct tttcgtctaa ctgcggcatc agcggctgaa      60
taatcagcac ggcaggtttg gtattcgtca ttttattgtc cattagcggt atttatttac     120
caccagccta acggagttat ttatgttacg gcgttgctgt tacttatttc gctaataaga     180
tcacgcatag cattattaac aatatttacc tggtgcgcat gaatacgcac cctacaaagt     240
caagtccctc gctggcgaac tcaccttacg cagtctacgg ttaatcaaaa agcataaaaa     300
tttcaccaac catggatagc cattatgacc acccatgtcg acaccacagc acatcagaca     360
agcgaactcc ttcagctgca gcaaatttta caggcgcatc ttgaacattt actgcctgcc     420
ggacagcaaa gcgatcgcgt gcgtgccgcg atgcgtgccg gaacgctggc gcagggcaaa     480
cgtattcgtc ctttattact gctgctggca gcgcgcgata tgggttgcga gctgacgcaa     540
aatggcgttc tcgatctcgc ctgtgcagtg gaaatggtgc acgcggcatc gctgattctg     600
gatgacattc cctcgatgga taacgcgcag atgcgtcgtg gtcgccctac cgtgcatcgc     660
gaatttggtg aaaacgtggc gattctcgcc gccatcgcgc tgcttagccg cgcatttgaa     720
gtgattgcca ttgcacccgg tttgcctgcc atacataaat ctgaagcgat tgctgaactc     780
tccgctgccg tcggcctgca gggcttagtg caagggcaat tccaggatct gcacgacggc     840
acgcagagcc gcagcccgga agcgatcgcc atgaccaacg aactgaaaac cagcgtgctg     900
tttcgcgcca cgctgcaaat ggcggcgatt gccgctgacg cttcaccgca ggtgcggcaa     960
agacttagct tcttcgccca ggatttgggc caggcgtttc aactgctcga cgacctcgcc    1020
gacggttgca aacacaccgg taaagatgtg caccaggatc agggcaaatc cacgctggta    1080
cagatgctcg gtgctgacgg cgcggaacgt cgcctgcgcg atcacctgcg cagcgcagat    1140
gcacaccttg cctgcgcctg ccatcgcggc atcgccactc gccaatatat gcacgcgctg    1200
tttaatcaac agctagcgat attcaactga gcgcggctca gccggtgggc cactttgcgg    1260
tgatcgcgcc gccgctctac agccactttc acgcgttgca ggcgttagca caaacgctgc    1320
tggcgcgcgg ccatcgcatc acattcatcc agcaagccga tgcccgcact ttgcttagcg    1380
acgaacgcat cgattttgtt gccgtcggcc aacagacgca tcctgccggt tcgctggcgc    1440
ccgtgttgca tcggctggcc tcgccgggcg gcctgtcgct gtttcgcgtg atcgacgatc    1500
tcgcgtcctg caccgatatg ctgtgccgcg aactgcctgc ggtactgaaa gcattgaaca    1560
tcgatggcgt gatcgccgac gaaatggaag cggcgggcgg attggtcgct gaagcgctgc    1620
atctgccgtt tgtttcggtg gcctgcgcct tgccggtcaa tcgtgaagcc gggattccgc    1680
ttgcggtgat gcccttccgt tttgcacagg atgacaaagc gctgaaacgt tttcaggcca    1740
gcagcgatat ctatgatcgc atcatgcgtc gtcacggcga cgtgatcctc aaacacgcgc    1800
gggcgtttaa tttgacggag cggcgcggat tacatcagtg cctgtcgccg ctggcacaaa    1860
tcagccagat ggtgccggcc tttgattttc cacgtcagca actgcccgcc tgctatcacg    1920
ccgtggggcc actccgcgcc ccggtttctc ctgcgccgct ccatgcgccc tggccagcgc    1980
tgcgtcagcc ggtggtttat gcctcgctgg gtacgctgca aggccatcgc ttccggctgt    2040
ttctgcatct ggcgcaggcg tgccgccagc tgcggctatc gctggtgatc gcccattgtg    2100
ggggattaaa cgccgaacag acgcatcagc tggagctcgc tggcgcggcg tgggtgacgg    2160
atttcgtcga tcagcgcgca gccctacagc acgcgcagct gtttatcact catgccgggt    2220 taaacgcgc gctggaagca ctggaatgcg gtacgccgat gctggcgctg ccgattgctt    2280
ttgatcagcc cggcgtggcg gcgcgcattg agtggcatga cgttggtcgc cgcgcatcac    2340
```

```
gctttagccg tgttcatcaa ctggagcagc atctgcaaca gctgctgacc gacgatcgtt   2400
acgcgctacg gatgtcagcg attcaggcgc agctgcagcc cgcaggcggt tgccagcgtg   2460
ccgccgacat cgtcgagcag gcgctgtgcc agcagcaagt cgtgctggcg gaggcgacct   2520
gatgcgcacg caatacgatg tgattttggt cggtgctgga ctggcgaatg gcttgattgc   2580
gctgcgtctg cgtcaattgc agccacaact gaaatgcctg ttgctggaga gcgatgcgca   2640
tccggcaggc aatcatacct ggtcgtttca tcacagcgat ctcagcgccg aacaacttcg   2700
ctggctgcaa ccgctgatta ccgtgcgttg gtcaggttat caggtgcgtt ttcctgcgct   2760
gcgccgcaat ctggacgggg attattgttc catcgcatca ggcgattttg cccgccatct   2820
ttacgcggcg atgggtgacg atctgtggac aaacacagcc gtacaacagg taaacccac   2880
gcaggtgacg ctggcggatg gccgtgaact tgctgcgcaa gtggtgattg atggtcgcgg   2940
cctgcagccg acgccacatc tgcagctggg ttatcaggtg tttcttggac aagagtggca   3000
gctggcgcag ccgcacggcc tgcagcagcc gatcctgatg gatgccaccg tcgatcagca   3060
agcgggttat cgttttgtct acacgctgcc gctcagcgcc gatcggctat tgattgaaga   3120
tacccattac gttaaccagc ccgcgctggc ggagaacacc gctcgtcagc acatcgccga   3180
ctatgccaat cagcaaggct ggacgctgag tacgctgctg cgtgaagagc acggcatatt   3240
accgattacc ctgagcggca acatcgatcg attctggcaa cagcagcgcg gccaagcgtg   3300
cagcggcctg cgcgccgggc tgtttcatgc caccaccggt tactccttgc cgtccgccgt   3360
ggcgctagcg gagttggtag cagcgctgtt gcccaccgat gccctcacgc tcagccaaca   3420
tatcgaacgc tttgcccgtc agcagtggcg cgaacagcga ttttccgtc tgctaaaccg   3480
catgctgttt ttggccggta agccgcagca gcgctggcgc gtgatgcaac gtttttaccg   3540
gctcgatgcc gggttaatta ccgctttta cgccgggcaa ctgcgcctgc gcgataaaac   3600
gcggattctg tgcggcaagc cgccggtgcc catcggtgaa gcgctgcgcg cgctgttgaa   3660
ttctgtcgaa ccagggaaga aaaaatgaaa cgcacttatg tgattggcgc aggctttggc   3720
ggcctggcgc tggcgattcg cctgcaagcg gcgggcatac caaccaccttt actcgagcag   3780
cgcgacaaac cgggcggacg cgcctatgtg tttgaggaca gtggctttac cttcgatgcc   3840
ggacccacgg tgatcaccga tcccagcgcc atcgaagagt tgttcacgct ggcaggaaaa   3900
tcgctcagcg attacgtcga gctgatgccg gtaacgccct tctatcgcct gtgctgggaa   3960
gatggcaaac agcttgatta cgacaataat cagccgctgc tggagcagca gatcgccacg   4020
ttcaatccgc aagatgtaga aggctatcgt caatttcttg cctattcacg tgaagtattt   4080
agagagggtt atctgaaact cggcacggtg ccgtttctgc aggtgcgtga catgctgcgc   4140
gtcgcgccgc agttgggacg tctgcaagca tggcgcagca tctacagcat ggtggcgaaa   4200
tttattcagg acgatcatct gcgtcaggcg ttttccttcc actcattgct ggtgggcggt   4260
aatcctttg caacgtcatc gatctatacc ttaattcatg cgctggagcg tgaatggggc   4320
gtgtggtttc cgcgcggcgg caccggcgcg ctggtgcagg gcatggcgcg actgttcgag   4380
gacttgggcg gcgagctgtt actgaatgcc gaagtgagcc agctggaaac cagcggcaat   4440
cgcattagcg gcgttcagtt agagggcgga cgacgcttcg atgccgccgc tgtggcctcc   4500
aatgccgacg tggtgcatac ctacgacaaa ctgcttcgcc accatccgct ggcaatgaaa   4560
cgtgcgacat cgctgaagcg taagcgcatg agcaactcgc tgtttgtact ctattttggc   4620
ctgaatcagc cgcatgaaca gctcgcgcac acaccgtct gttttggccc gcgttatcgt   4680
gagttgatcg atgagatttt caacagcagc cagctggcag acgattttc actttacctg   4740
```

```
cacgcgccct gcagcagcga tccgtcgctg gcaccgcccg gctgcggcag ctttttatgtg    4800 ttagcgccgg tgccgcatct cggcaccgct gacatcgact ggcaacagga aggaccgcgc    4860
ttgcgcgatc gaattttttgc ttatctggag cagcactaca tgccgggatt acgtcagcaa    4920
ttagtgacac acagaatgtt tacgccgttt gattttcgcg acacgctgca tgcccatcac    4980
ggctcggcgt tttcgctgga gccgattttg acgcaaagcg cctggttccg cccgcataac    5040
cgcgatgccg atatcagcaa tctctatctg gtgggtgccg gtacgcatcc aggcgcgggc    5100
gtgcccggcg tgatcggttc ggccaaggcc accgccaggc tgatgctgga ggatcgcgcc    5160
gaatgaatcg acagccttta cttgagcaag taacgcaaac catggcggtg ggctcgaaga    5220
gtttcgccac cgccgccaag ctgtttgatg caccgacgcg ccgcagcacg ctgatgctgt    5280
atgcgtggtg tcgtcactgc gatgatgtga ttgatgggca aacgctgggc gaaggcggca    5340
cgcagcatgc cgtcgaagac gcgcaggcac gtatgcagca tctgcaaatt gaaacccgcc    5400
gcgcctacag cggcgcgcac atggatgaac cggcgtttag ggcgtttcag gaagtggcga    5460
tcattcacca gctgccgcaa caactggcgt ttgatcatct ggaaggcttc gctatggatg    5520
cacgcaacga acattacgcg agcttcgatg acacgctgcg ttactgctat cacgtcgcgg    5580
gcgtggtcgg tttgatgatg gcgcgcgtaa tgggcgtgcg cgacgaagcg gtgctcgatc    5640
acgcctgcga tttaggactg gcgttccagc tcactaacat tgcgcgcgac attgtagaag    5700
atgccgaaaa tggtcgctgc tatctgccgc aatcctggct cgatcaggcg ggattacgcg    5760
ccgatacgct gactgcaccg caacatcgtg cagcgctcgc ctcactggca gcgcgtttag    5820
tggcggaggc ggaaccctat tatcactcgg cgcgatccgg tttaccgggt ttaccgctgc    5880
gctcggcgtg ggccatcgct acggctcgcg gcgtttatcg cgaaattggc gtcaaagttc    5940
agcacgccgg tgtgcacgcc tgggattcac ggcagcgcac cagtaaaggt gaaaaactgg    6000
cgctgctggt gaaaggggca ggtttggcga tcacttcgcg tgtgtctcgt cctgaaccgc    6060
gtccggctgg tctgtggcag cgtcctcgtt gattttacgt ccgtgacgct ggcgcagcgt    6120
ggcttgcagc ttattcagcg gtggcgcgta gaggaaacca aacgacacgc agccttcacg    6180
cccgcgcacc gcatgatgca tgcggtgcgc catgtataag cgcttaagat agcctttgcg    6240
cgggatatag cggaacggcc agcgttgatg caccaggcca tcgtgcacca tgaagtagag    6300
cgcgccgtac gtcgtcattc cggcaccaat ccactgcagc ggccacatgc cttgcacacc    6360
gacataaatc agcacaatcg ccagtaccgc aaacaccacc gcataaagat cgttgagctc    6420
aaacttaccg ctgtgcggtt catggtgcga cagatgccag ccccatcccc aaccgtgcat    6480
gatgtattta tgcgacagcg ccgctacgat ttccatcacc accacggttg ccaacaagat    6540
aagcacgttc cataaccaga gcattgttcg tccatttgtg gaaaagggaa gtactaaagg    6600
tggacgcgga tgagtgatgg cgcaaggttt accatgttta gaaatttttaa aagtccataa    6660 cacgttatga acgctgcatt gcagaaagcg cagatttcac acatactcac cacacttatc    6720
aatacacgtg ttaactacat gggggattta tgccttctac agccgtaaga caaaaaaaaa    6780
ctgtcagtgt gacacttgaa cctgctctac tcgagcaagc cagagaggca gggctcaatt    6840
tatccgccat cctatccaaa gctttgcaac atgaaattcg cacgactgca gcagaaagat    6900
ggaagcgtga aaacagtgaa ggtttgcagg aactcaatcg cataaccgaa gagcacggtt    6960
tattgtcgga tgaatacagg acgttttaga catgcaata                            6999
```

<210> SEQ ID NO 19

```
<211> LENGTH: 31
<212> TYPE: DNA
<213> ORGANISM: artificial sequence
<220> FEATURE:
<223> OTHER INFORMATION: Primer pWEB260F

<400> SEQUENCE: 19
gaattcacca accatggata gccattatga c                              31

<210> SEQ ID NO 20
<211> LENGTH: 26
<212> TYPE: DNA
<213> ORGANISM: artificial sequence
<220> FEATURE:
<223> OTHER INFORMATION: Primer pWEB260R

<400> SEQUENCE: 20
gaattcaacg aggacgctgc cacaga                                    26
```

GENES ENCODING CAROTENOID COMPOUNDS

This application claims the benefit of U.S. Provisional Application No. 60/471,904 filed May 20, 2003 and U.S. Provisional Application No. 60/527,083 filed Dec. 3, 2003, the disclosures of which are hereby incorporated by reference.

FIELD OF THE INVENTION

The invention relates to the field of molecular biology and microbiology. More specifically, this invention pertains to nucleic acid fragments isolated from a novel strain of bacteria belonging to the Enterobacteriaceae family encoding enzymes useful for microbial production of carotenoid compounds (e.g., lycopene, β-carotene, zeaxanthin, and zeaxanthin-β-glucosides).

BACKGROUND OF THE INVENTION

Carotenoids represent one of the most widely distributed and structurally diverse classes of natural pigments, producing pigment colors of light yellow to orange to deep red color. Eye-catching examples of carotenogenic tissues include carrots, tomatoes, red peppers, and the petals of daffodils and marigolds. Carotenoids are synthesized by all photosynthetic organisms, as well as some bacteria and fungi. These pigments have important functions in photosynthesis, nutrition, and protection against photooxidative damage. For example, animals do not have the ability to synthesize carotenoids but must obtain these nutritionally important compounds through their dietary sources.

Industrially, only a few carotenoids are used for food colors, animal feeds, pharmaceuticals, and cosmetics, despite the existence of more than 600 different carotenoids identified in nature. This is largely due to difficulties in production. Presently, most of the carotenoids used for industrial purposes are produced by chemical synthesis; however, these compounds are very difficult to make chemically (Nelis and Leenheer, *Appl. Bacteriol.* 70:181–191 (1991)). Natural carotenoids can either be obtained by extraction of plant material or by microbial synthesis; but, only a few plants are widely used for commercial carotenoid production and the productivity of carotenoid synthesis in these plants is relatively low. As a result, carotenoids produced from these plants are very expensive. One way to increase the productive capacity of biosynthesis would be to apply recombinant DNA technology (reviewed in Misawa and Shimada, *J. Biotech.* 59:169–181 (1998)). Thus, it would be desirable to produce carotenoids in non-carotenogenic bacteria and yeasts, thereby permitting control over quality, quantity and selection of the most suitable and efficient producer organisms. The latter is especially important for commercial production economics (and therefore availability) to consumers.

Structurally, the most common carotenoids are 40-carbon ($C_{40}$) terpenoids; however, carotenoids with only 30 carbon atoms ($C_{30}$; diapocarotenoids) are detected in some species. Biosynthesis of each of these types of carotenoids is derived from the isoprene biosynthetic pathway and its five-carbon universal isoprene building block, isopentenyl pyrophosphate (IPP). This biosynthetic pathway can be divided into two portions: 1) the upper isoprene pathway, which leads to the formation of farnesyl pyrophosphate (FPP); and 2) the lower carotenoid biosynthetic pathway, comprising various crt genes which convert FPP into long $C_{30}$ and $C_{40}$ carotenogenic compounds. Both portions of this pathway are shown in FIG. 1.

Typically, the formation of phytoene represents the first step unique to biosynthesis of $C_{40}$ carotenoids (FIGS. 1 and 2). Phytoene itself is a colorless carotenoid and occurs via isomerization of IPP to dimethylallyl pyrophosphate (DMAPP) by isopentenyl pyrophosphate isomerase. The reaction is followed by a sequence of 3 prenyltransferase reactions in which geranyl pyrophosphate (GPP), farnesyl pyrophosphate (FPP), and geranylgeranyl pyrophosphate (GGPP) are formed. The gene crtE, encoding GGPP synthetase, is responsible for this latter reaction. Finally, two molecules of GGPP condense to form phytoene (PPPP). This reaction is catalyzed by phytoene synthase (encoded by the gene crtB).

Lycopene is the first "colored" carotenoid produced from phytoene. Lycopene imparts the characteristic red color of ripe tomatoes and has great utility as a food colorant. It is also an intermediate in the biosynthesis of other carotenoids in some bacteria, fungi and green plants. Lycopene is prepared biosynthetically from phytoene through four sequential dehydrogenation reactions by the removal of eight atoms of hydrogen, catalyzed by the gene crtI (encoding phytoene desaturase). Intermediaries in this reaction are phytofluene, ζ-carotene, and neurosporene.

Lycopene cyclase (CrtY) converts lycopene to β-carotene, the second "colored" carotenoid. β-carotene is a typical carotene with a color spectrum ranging from yellow to orange. Its utility is as a colorant for margarine and butter, as a source for vitamin A production, and recently as a compound with potential preventative effects against certain kinds of cancers.

β-carotene is converted to zeaxanthin via a hydroxylation reaction resulting from the activity of β-carotene hydroxylase (encoded by the crtZ gene). For example, it is the yellow pigment that is present in the seeds of maize. Zeaxanthin is contained in feeds for hen or colored carp and is an important pigment source for their coloration. Finally, zeaxanthin can be converted to zeaxanthin-β-monoglucoside and zeaxanthin-β-diglucoside. This reaction is catalyzed by zeaxanthin glucosyl transferase (encoded by the crtX gene).

In addition to the carotenoid biosynthetic genes and enzymes responsible for creation of phytoene, lycopene, β-carotene, zeaxanthin, and zeaxanthin-β-glucosides, various other crt genes are known which enable the intramolecular conversion of $C_{40}$ compounds to produce numerous other functionalized carotenoid compounds by: (i) hydrogenation, (ii) dehydrogenation, (iii) cyclization, (iv) oxidation, (v) esterification/glycosylation, or any combination of these processes.

Many of the bacteria within family Enterobacteriaceae (which includes, but are not limited to the genera *Alterococcus, Arsenophonus, Brenneria, Buchnera, Budvicia, Buttiauxella, Cedecea, Citrobacter, Edwardsiella, Enterobacter, Erwinia, Escherichia, Ewingella, Hafnia, Klebsiella, Kluyvera, Leclercia, Leminorella, Moellerella, Morganella, Obesumbacterium, Pantoea, Pectobacterium, Photorhabdus, Plesiomonas, Pragia, Proteus, Providencia, Rahnella, Salmonella, Serratia, Shigella, Sodalis, Tatumella, Trabulsiella, Wigglesworthia, Xenorhabdus, Yersinia,* and *Yokenella*) are naturally pigmented, thus indicating the ability of these organisms to produce carotenoids. Several reviews discuss the genetics of carotenoid pigment biosynthesis, such as those of G. Armstrong (*J. Bact.* 176: 4795–4802 (1994); *Annu. Rev. Microbiol.* 51:629–659 (1997)). Carotenoid biosynthesis and the gene sequences encoding CrtE, X, Y, I, B, and Z have been particularly well-studied within the genus *Pantoea*, a small group of organisms previously classified within a broad group of bacteria all formerly known within the genus *Erwinia* (U.S. Pat. No. 5,656,472; U.S. Pat. No. 5,5545,816; U.S. Pat. No. 5,530,189; U.S. Pat. No. 5,530,188; U.S. Pat. No. 5,429,939; WO 02/079395 A2; see also GenBank® Accession Nos. M87280, D90087, AY166713, AB076662, respectively). (See Hauben et al., *Syst Appl. Microbiol.* 21(3):384–397 (August 1998), for details concerning the reclassification of the large former genus *Erwinia* into four phylogenetic groups comprised of *Erwinia, Pectobacterium, Brenneria* gen. nov., and *Pantoea*.) However, the existing literature provides limited information concerning gene sequences from other organisms within the family Enterobacteriaceae encoding crtEXYIBZ that are not included within the genus *Pantoea*.

The problem to be solved, therefore, is to identify nucleic acid sequences encoding all or a portion of the carotenoid biosynthetic enzymes from organisms classified within the family Enterobacteriaceae, but not classified within the genus *Pantoea*, to facilitate studies to better understand carotenoid biosynthetic pathways, provide genetic tools for the manipulation of those pathways, and provide a means to synthesize carotenoids in large amounts by introducing and expressing the appropriate gene(s) in an appropriate host. This will lead to carotenoid production superior to synthetic methods.

Applicants have solved the stated problem by isolating six unique open reading frames (ORFs) in the carotenoid biosynthetic pathway encoding CrtE, CrtX, CrtY, CrtI, CrtB and CrtZ enzymes from a yellow-pigmented bacterium belonging to the Enterobacteriaceae family, designated as strain DC260.

SUMMARY OF THE INVENTION

The invention provides six genes, isolated from strain DC260 that have been demonstrated to be involved in the synthesis of various carotenoids including lycopene, β-carotene, zeaxanthin, and zeaxanthin-β-glucosides. The genes are clustered on the same operon and include the crtE, crtX, crtY, crtI, crtB and crtZ genes. The DNA sequences of the crtE, crtX, crtY, crtI, crtB and crtZ genes correspond to ORFs 1–6 and SEQ ID NOs:1, 3, 5, 7, 9 and 11; respectively.

Accordingly, the invention provides an isolated nucleic acid molecule encoding a carotenoid biosynthetic enzyme, selected from the group consisting of:
(a) an isolated nucleic acid molecule encoding the amino acid sequence selected from the group consisting of SEQ ID NOs:2, 4, 6, 8, 10, and 12;
(b) an isolated nucleic acid molecule that hybridizes with (a) under the following hybridization conditions: 0.1× SSC, 0.1% SDS, 65° C. and washed with 2×SSC, 0.1% SDS followed by 0.1×SSC, 0.1% SDS; and
(c) an isolated nucleic acid molecule that is complementary to (a) or (b).

The invention additionally provides polypeptides encoded by the instant genes and genetic chimera comprising suitable regulatory regions for genetic expression of the genes in bacteria, yeast, filamentous fungi, algae, and plants as well as transformed hosts comprising the same.

Similarly the invention provides an isolated nucleic acid molecule as set forth in SEQ ID NO:18, comprising the crtE, crtX, crtY, crtI, crtB and crtZ, genes or an isolated nucleic acid molecule having at least 95% identity to SEQ ID NO:18, wherein the isolated nucleic acid molecule encodes all of the polypeptides crtE, crtX, crtY, crtI, crtB and crtZ.

The invention provides a method of obtaining a nucleic acid molecule encoding a carotenoid biosynthetic enzyme comprising:
(a) probing a genomic library with the present nucleic acid molecules;
(b) identifying a DNA clone that hybridizes with the present nucleic acid molecules; and
(c) sequencing the genomic fragment that comprises the clone identified in step (b), wherein the sequenced genomic fragment encodes a carotenoid biosynthetic enzyme.

Similarly, the invention provides a method of obtaining a nucleic acid molecule encoding a carotenoid biosynthetic enzyme comprising:
(a) synthesizing at least one oligonucleotide primer corresponding to a portion of the present nucleic acid sequences; and
(b) amplifying an insert present in a cloning vector using the oligonucleotide primer of step (a);

wherein the amplified insert encodes a portion of an amino acid sequence encoding a carotenoid biosynthetic enzyme.

In a preferred embodiment, the invention provides a method for the production of carotenoid compounds comprising:
(a) providing a transformed host cell comprising:
 (i) suitable levels of farnesyl pyrophosphate; and
 (ii) a set of nucleic acid molecules encoding the present carotenoid enzymes under the control of suitable regulatory sequences;
(b) contacting the host cell of step (a) under suitable growth conditions with an effective amount of a fermentable carbon substrate whereby a carotenoid compound is produced.

In a specific preferred embodiment, the invention provides a method for the production of carotenoid compounds in a C1 metabolizing host, for example a high growth methanotrophic bacterial strain such as *Methylomonas* 16a (ATCC designation PTA 2402), wherein the C1 metabolizing host:
(a) grows on a C1 carbon substrate selected from the group consisting of methane and methanol; and
(b) comprises a functional Embden-Meyerhof carbon pathway, said pathway comprising a gene encoding a pyrophosphate-dependent phosphofructokinase enzyme.

Additionally, the invention provides a method of regulating carotenoid biosynthesis in an organism comprising overexpressing at least one carotenoid gene selected from the group consisting of SEQ ID NOs:1, 3, 5, 7, 9, and 11 in an organism such that the carotenoid biosynthesis is altered in the organism.

In an alternate embodiment, the invention provides a mutated gene encoding a carotenoid enzyme having an altered biological activity produced by a method comprising the steps of:
(i) digesting a mixture of nucleotide sequences with restriction endonucleases wherein said mixture comprises:
 a) an isolated nucleic acid molecule encoding a carotenoid biosynthetic enzyme selected from the group consisting of SEQ ID NOs:1, 3, 5, 7, 9, and 11;
 b) a first population of nucleotide fragments which will hybridize to said isolated nucleic acid molecules of step (a); and c) a second population of nucleotide fragments which will not hybridize to said isolated nucleic acid molecules of step (a);

wherein a mixture of restriction fragments are produced;
(ii) denaturing said mixture of restriction fragments;
(iii) incubating the denatured said mixture of restriction fragments of step (ii) with a polymerase; and
(iv) repeating steps (ii) and (iii) wherein a mutated carotenoid gene is produced encoding a protein having an altered biological activity.

In another embodiment, the invention provides a strain DC260 comprising the 16S rDNA sequence as set forth in SEQ ID NO:16.

BRIEF DESCRIPTION OF THE DRAWINGS, SEQUENCE DESCRIPTIONS, AND BIOLOGICAL DEPOSITS

The patent or application file contains at least one drawing executed in color. Copies of this patent or patent application publication with color drawing(s) will be provided by the Office upon request and payment of the necessary fee.

Figure 3:
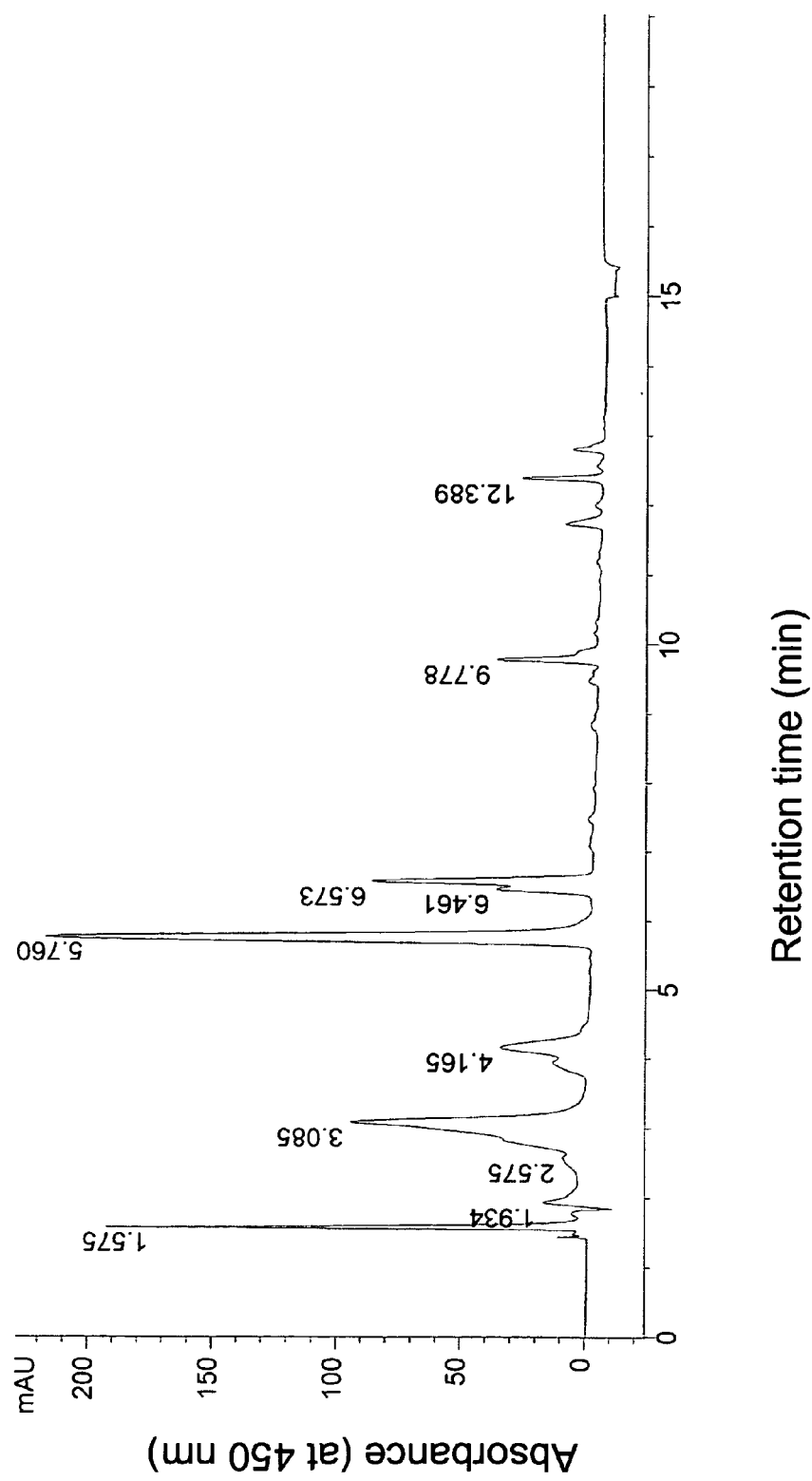

FIG. 3 presents results of an HPLC analysis of the carotenoids contained within strain DC260.

Figure 4:
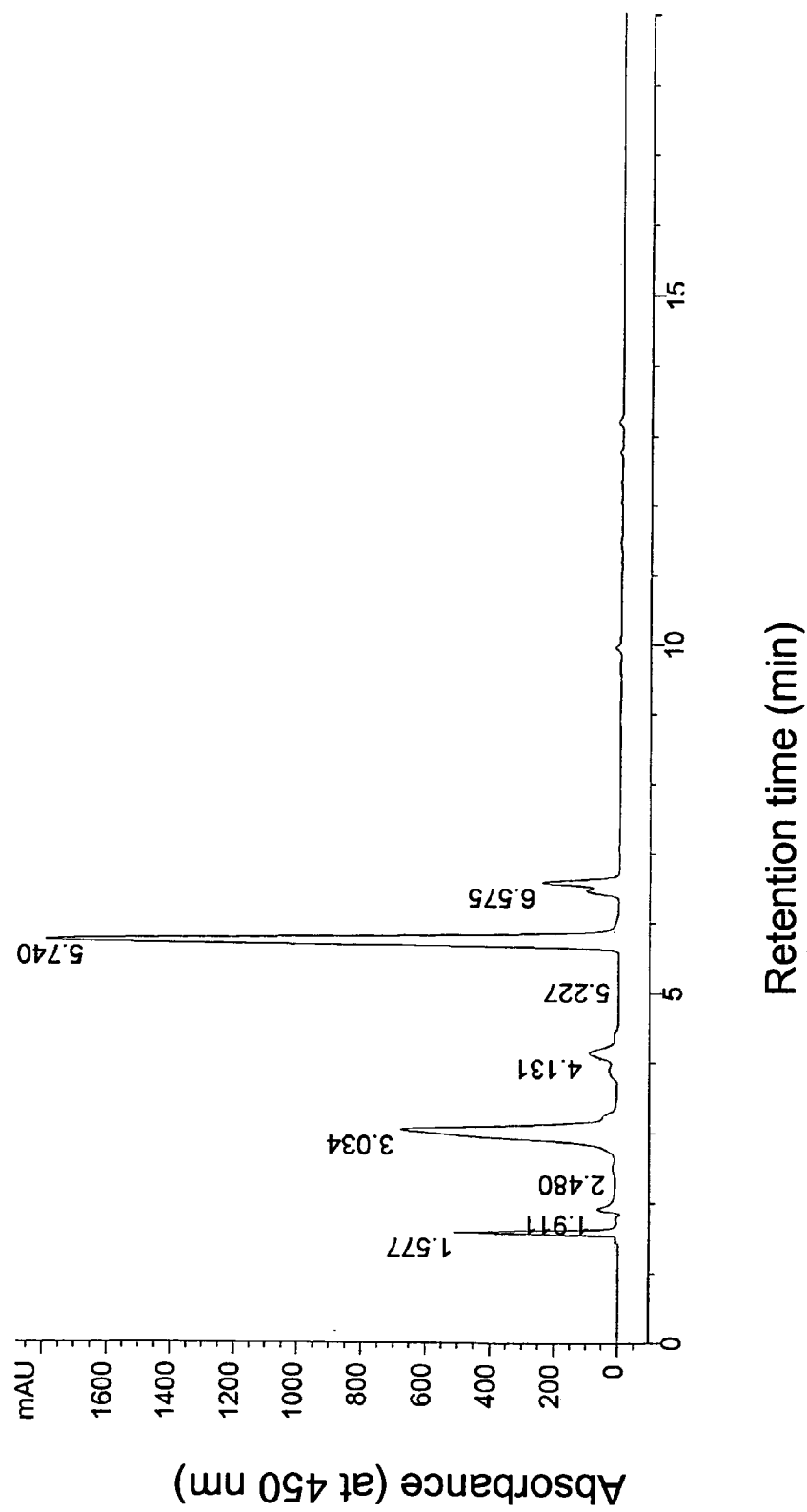

FIG. 4 presents results of an HPLC analysis of the carotenoids contained within transformant E. coli comprising cosmid pWEB-260.

Figure 5:
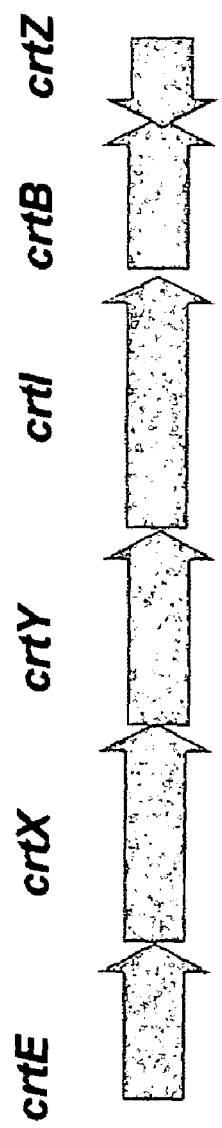

FIG. 5 shows a gene cluster containing the carotenoid biosynthesis genes crtEXYIBZ.

Figure 6:
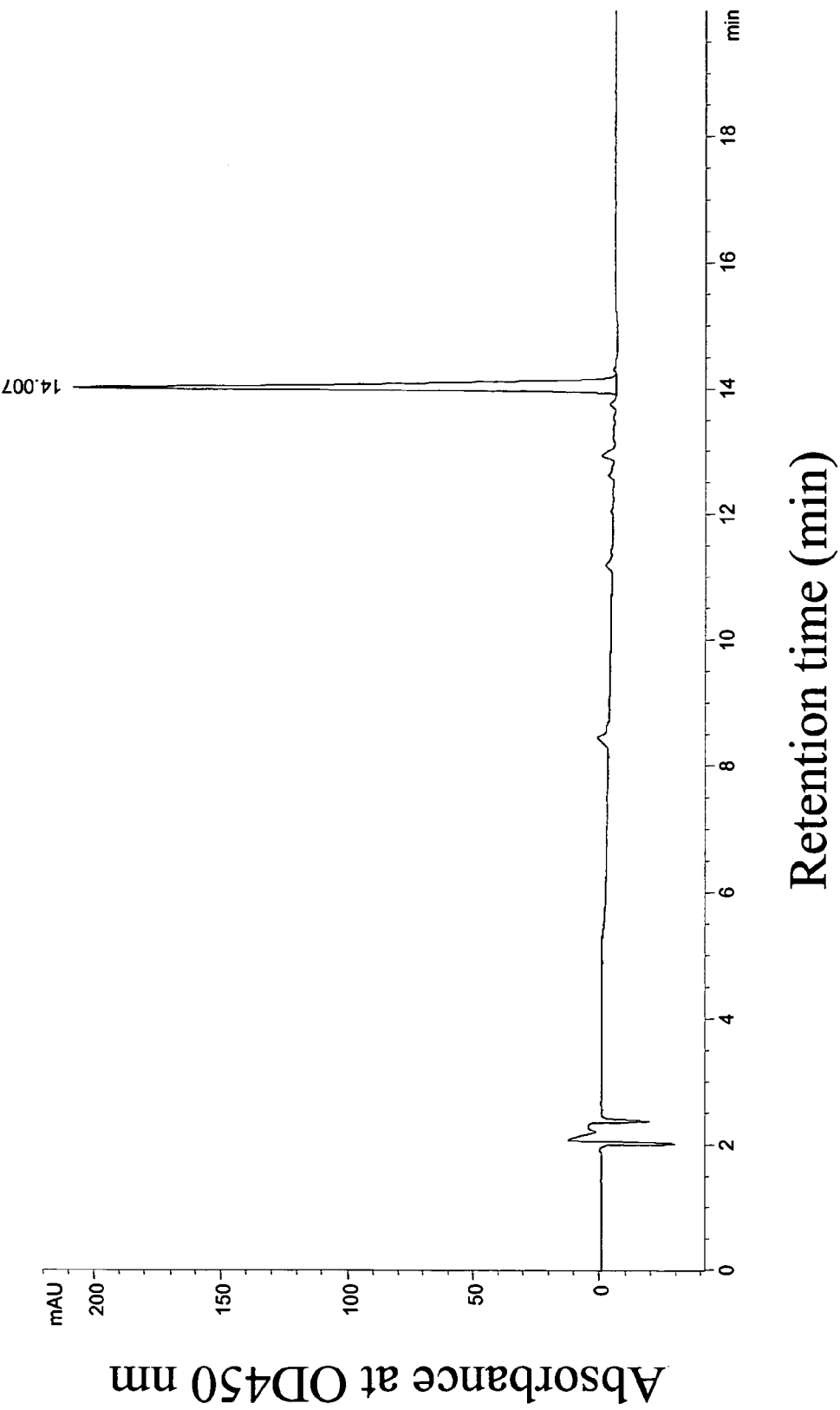

FIG. 6 shows the HPLC analysis of the carotenoids from Methylomonas 16a MWM1000 (ald$^-$/CrtN1$^-$) strain containing pDCQ329.

The invention can be more fully understood from the following detailed description and the accompanying sequence descriptions that form a part of this application.

The following sequences are conform with 37 C.F.R. 1.821–1.825 ("Requirements for Patent Applications Containing Nucleotide Sequences and/or Amino Acid Sequence Disclosures—the Sequence Rules") and consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NOs:1–12 are full length genes or proteins as identified in Table 1.

TABLE 1

Summary of Strain DC260 Gene and Protein SEQ ID Numbers

| Description | ORF No. | Nucleic acid SEQ ID NO. | Peptide SEQ ID NO. |
|---|---|---|---|
| crtE | 1 | 1 | 2 |
| crtX | 2 | 3 | 4 |
| crtY | 3 | 5 | 6 |
| crtI | 4 | 7 | 8 |
| crtB | 5 | 9 | 10 |
| crtZ | 6 | 11 | 12 |

SEQ ID NOs:13–15, and 17 are the nucleotide sequences encoding primers HK12, JCR14, JCR15, and TET-1 FP-1; respectively.

SEQ ID NO:16 provides the 16S rRNA gene sequence of strain DC260.

SEQ ID NO:18 is the nucleotide sequence of a 6,999 bp fragment of DNA from strain DC260 encoding the crtE, crtX, crtY, crtI, crtB and crtZ genes.

SEQ ID NO:19 is the nucleic acid sequence of primer pWEB260F.

SEQ ID NO:20 is the nucleic acid sequence of primer pWEB260R.

Applicants made the following biological deposit under the terms of the Budapest Treaty on the International Recognition of the Deposit of Micro-organisms for the Purposes of Patent Procedure:

| Depositor Identification Reference | International Depository Designation | Date of Deposit |
|---|---|---|
| Methylomonas 16a | ATCC PTA 2402 | Aug. 22, 2000 |

As used herein, "ATCC" refers to the American Type Culture Collection International Depository Authority located at ATCC, 10801 University Blvd., Manassas, Va. 20110-2209, U.S.A. The "International Depository Designation" is the accession number to the culture on deposit with ATCC.

The listed deposit will be maintained in the indicated international depository for at least thirty (30) years and will be made available to the public upon the grant of a patent disclosing it. The availability of a deposit does not constitute a license to practice the subject invention in derogation of patent rights granted by government action.

DETAILED DESCRIPTION OF THE INVENTION

The genes of this invention and their expression products are useful for the creation of recombinant organisms that have the ability to produce various carotenoid compounds. Nucleic acid fragments encoding CrtE, CrtX, CrtY, CrtI, CrtB, and CrtZ have been isolated from strain DC260 and identified by comparison to public databases containing nucleotide and protein sequences using the BLAST and FASTA algorithms well known to those skilled in the art. The genes and gene products of the present invention may be used in a variety of ways for the enhancement or manipulation of carotenoid compounds.

There is a general practical utility for microbial production of carotenoid compounds as these compounds are very difficult to make chemically (Nelis and Leenheer, Appl. Bacteriol. 70:181–191 (1991)). Most carotenoids have strong color and can be viewed as natural pigments or colorants. Furthermore, many carotenoids have potent antioxidant properties and thus inclusion of these compounds in the diet is thought to be healthful. Well-known examples are β-carotene, canthaxanthin, and astaxanthin. Additionally, carotenoids are required elements of aquaculture. Salmon and shrimp aquacultures are particularly useful applications for this invention as carotenoid pigmentation is critically important for the value of these organisms (Shahidi, F., and Brown, J. A., Critical reviews in Food Science 38(1): 1–67 (1998)). Finally, carotenoids have utility as intermediates in the synthesis of steroids, flavors and fragrances and compounds with potential electro-optic applications.

The disclosure below provides a detailed description of the isolation of carotenoid synthesis genes from strain DC260, modification of these genes by genetic engineering, and their insertion into compatible plasmids suitable for cloning and expression in *E. coli*, bacteria, yeasts, fungi and higher plants.

Definitions

In this disclosure, a number of terms and abbreviations are used. The following definitions are provided.

"Open reading frame" is abbreviated ORF.

"Polymerase chain reaction" is abbreviated PCR.

"High Performance Liquid Chromatography" is abbreviated HPLC.

The term "isoprenoid compound" refers to compounds formally derived from isoprene (2-methylbuta-1,3-diene; $CH_2\!=\!C(CH_3)CH\!=\!CH_2$), the skeleton of which can generally be discerned in repeated occurrence in the molecule. These compounds are produced biosynthetically via the isoprenoid pathway beginning with isopentenyl pyrophosphate (IPP) and formed by the head-to-tail condensation of isoprene units, leading to molecules which may be—for example—of 5, 10, 15, 20, 30, or 40 carbons in length.

Figure 1:
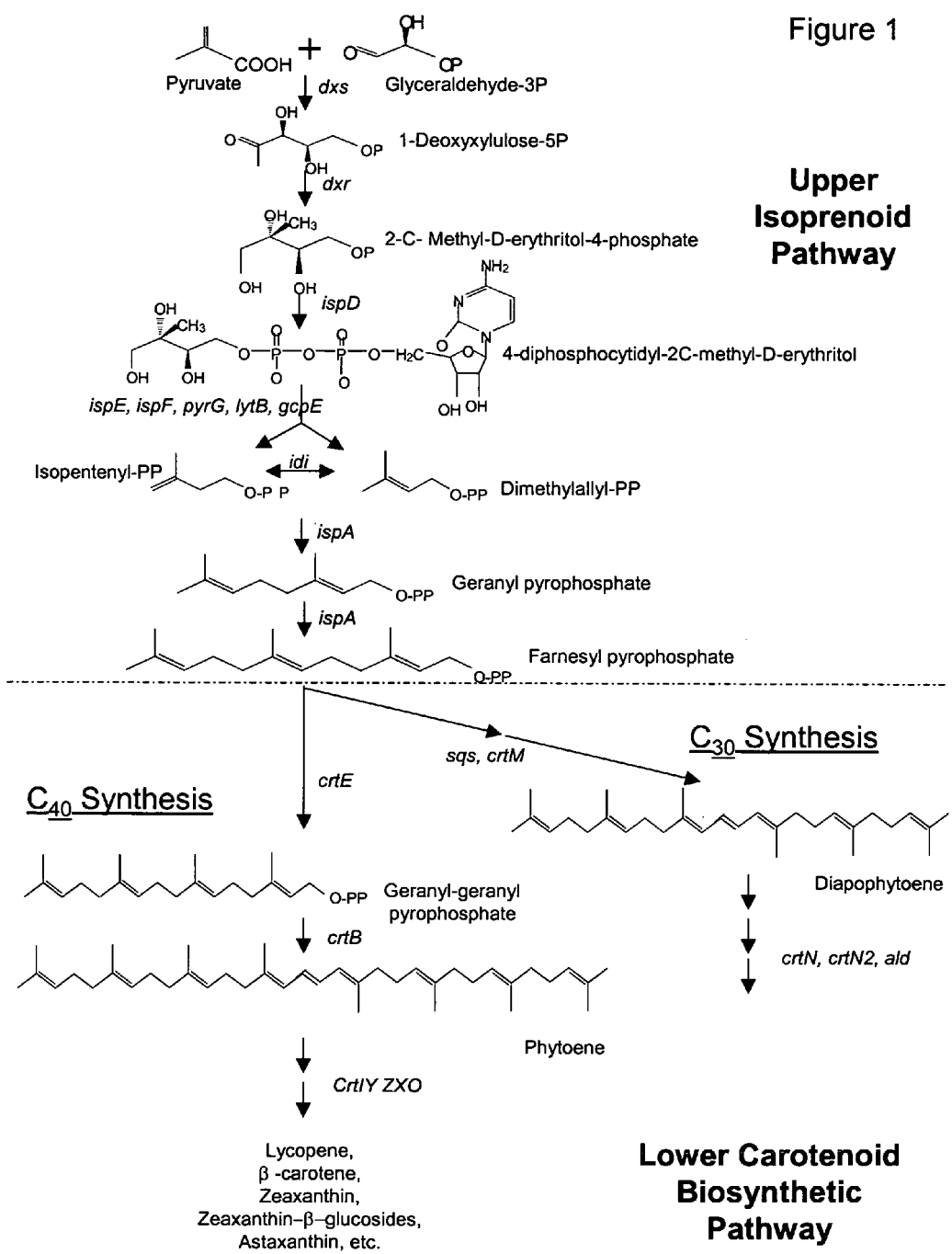
FIG. 1 shows the upper isoprenoid and lower carotenoid biosynthetic pathways.

The term "carotenoid biosynthetic pathway" refers to those genes comprising members of the upper isoprenoid pathway and/or lower carotenoid pathway of the present invention, as illustrated in FIG. 1.

The terms "upper isoprenoid pathway" and "upper pathway" will be use interchangeably and will refer to enzymes involved in converting pyruvate and glyceraldehyde-3-phosphate to farnesyl pyrophosphate (FPP). These enzymes include, but are not limited to: the "dxs" gene (encoding 1-deoxyxylulose-5-phosphate synthase); the "dxr" gene (encoding 1-deoxyxylulose-5-phosphate reductoisomerase); the "ispD" gene (encoding a 2C-methyl-D-erythritol cytidyltransferase enzyme; also known as ygbP); the "ispE" gene (encoding 4- diphosphocytidyl-2-C-methylerythritol kinase; also known as ychB); the "ispF" gene (encoding a 2C-methyl-d-erythritol 2,4-cyclodiphosphate synthase; also known as ygbB); the "pyrG" gene (encoding a CTP synthase); the "lytB" gene involved in the formation of dimethylallyl diphosphate; the "gcpE" gene involved in the synthesis of 2-C-methyl-D-erythritol 4-phosphate; the "idi" gene (responsible for the intramolecular conversion of IPP to dimethylallyl pyrophosphate); and the "ispA" gene (encoding geranyltransferase or farnesyl diphosphate synthase) in the isoprenoid pathway.

The terms "lower carotenoid biosynthetic pathway" and "lower pathway" will be used interchangeably and refer to those enzymes which convert FPP to a suite of carotenoids. These include those genes and gene products that are involved in the immediate synthesis of either diapophytoene (whose synthesis represents the first step unique to biosynthesis of $C_{30}$ carotenoids) or phytoene (whose synthesis represents the first step unique to biosynthesis of $C_{40}$ carotenoids). All subsequent reactions leading to the production of various $C_{30}$–$C_{40}$ carotenoids are included within the lower carotenoid biosynthetic pathway. These genes and gene products comprise all of the "crt" genes including, but not limited to: crtM, crtN, crtN2, crtE, crtX, crtY, crtI, crtB, crtZ, crtW, crtO, crtA, crtC, crtD, crtF, and crtU. Finally, the term "carotenoid biosynthetic enzyme" is an inclusive term referring to any and all of the enzymes in the present pathway including, but not limited to: CrtM, CrtN, CrtN2, CrtE, CrtX, CrtY, CrtI, CrtB, CrtZ, CrtW, CrtO, CrtA, CrtC, CrtD, CrtF, and CrtU.

For the present application, the term "carotenoid compound" is defined as a class of hydrocarbons having a conjugated polyene carbon skeleton formally derived from isoprene. This class of molecules is composed of triterpenes ($C_{30}$ diapocarotenoids) and tetraterpenes ($C_{40}$ carotenoids) and their oxygenated derivatives; and, these molecules typically have strong light absorbing properties and may range in length in excess of $C_{200}$. Other "carotenoid compounds" are known which are $C_{35}$, $C_{50}$, $C_{60}$, $C_{70}$, and $C_{80}$ in length, for example.

"$C_{30}$ diapocarotenoids" consist of six isoprenoid units joined in such a manner that the arrangement of isoprenoid units is reversed at the center of the molecule so that the two central methyl groups are in a 1,6-positional relationship and the remaining nonterminal methyl groups are in a 1,5-positional relationship. All $C_{30}$ carotenoids may be formally derived from the acyclic $C_{30}H_{42}$ structure, having a long central chain of conjugated double bonds, by: (i) hydrogenation (ii) dehydrogenation, (iii) cyclization, (iv) oxidation, (v) esterification/glycosylation, or any combination of these processes.

"Tetraterpenes" or "$C_{40}$ carotenoids" consist of eight isoprenoid units joined in such a manner that the arrangement of isoprenoid units is reversed at the center of the molecule so that the two central methyl groups are in a 1,6-positional relationship and the remaining nonterminal methyl groups are in a 1,5-positional relationship. All $C_{40}$ carotenoids may be formally derived from the acyclic $C_{40}H_{56}$ structure (Formula I below), having a long central chain of conjugated double bonds, by (i) hydrogenation, (ii) dehydrogenation, (iii) cyclization, (iv) oxidation, (v) esterification/glycosylation, or any combination of these processes. This class also includes certain compounds that arise from rearrangements of the carbon skeleton (Formula I), or by the (formal) removal of part of this structure.

Formula I

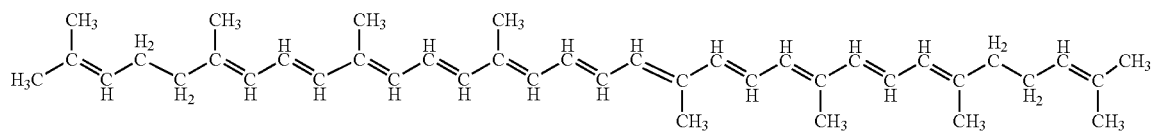

(I)

For convenience, carotenoid formulae are often written in a shorthand form as (Formula IA below):

Formula IA

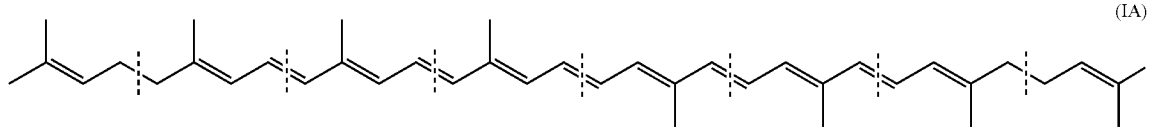

where the broken lines indicate formal division into isoprenoid units.

The term "functionalized" or "functionalization" refers to the (i) hydrogenation, (ii) dehydrogenation, (iii) cyclization, (iv) oxidation, or (v) esterification/glycosylation of any portion of the carotenoid backbone. This backbone is defined as the long central chain of conjugated double bonds. Functionalization may also occur by any combination of the above processes.

The term "CrtE" refers to a geranylgeranyl pyrophosphate synthase enzyme encoded by the crtE gene and which converts trans-trans-farnesyl diphosphate and isopentenyl diphosphate to pyrophosphate and geranylgeranyl diphosphate. A representative crtE gene is provided as SEQ ID NO:1.

The term "CrtX" refers to a zeaxanthin glucosyl transferase enzyme encoded by the crtX gene and which converts to zeaxanthin to zeaxanthin-β-diglucoside. A representative crtX (gene is provided as SEQ ID NO:3.

The term "CrtY" refers to a lycopene cyclase enzyme encoded by the crtY gene which converts lycopene to β-carotene. A representative crtY gene is provided as SEQ ID NO:5.

The term "CrtI" refers to a phytoene desaturase enzyme encoded by the crtI gene. CrtI converts phytoene into lycopene via the intermediaries of phytofluene, ζ-carotene and neurosporene by the introduction of 4 double bonds. A representative crtI gene is provided as SEQ ID NO:7.

The term "CrtB" refers to a phytoene synthase enzyme encoded by the crtB gene which catalyzes the reaction from prephytoene diphosphate to phytoene. A representative crtB gene is provided as SEQ ID NO:9.

The term "CrtZ" refers to a β-carotene hydroxylase enzyme encoded by the crtZ gene which catalyzes a hydroxylation reaction from β-carotene to zeaxanthin. A representative crtZ gene is provided as SEQ ID NO:11.

The term "Embden-Meyerhof pathway" refers to the series of biochemical reactions for conversion of hexoses such as glucose and fructose to important cellular 3-carbon intermediates such as glyceraldehyde 3-phosphate, dihydroxyacetone phosphate, phosphoenol pyruvate and pyruvate. These reactions typically proceed with net yield of biochemically useful energy in the form of ATP. The key enzymes unique to the Embden-Meyerof pathway are the phosphofructokinase and fructose 1,6-bisphosphate aldolase.

The term "Entner-Douderoff pathway" refers to a series of biochemical reactions for conversion of hexoses such as glucose or fructose to the important 3-carbon cellular intermediates pyruvate and glyceraldehyde 3-phosphate without any net production of biochemically useful energy. The key enzymes unique to the Entner-Douderoff pathway are the 6-phosphogluconate dehydratase and a ketodeoxyphosphogluconate aldolase.

The term "$C_1$ carbon substrate" or "single carbon substrate" refers to any carbon-containing molecule that lacks a carbon-carbon bond. Examples are methane, methanol, formaldehyde, formic acid, formate, methylated amines (e.g., mono-, di-, and tri-methyl amine), methylated thiols, and carbon dioxide.

The term "$C_1$ metabolizer" refers to a microorganism that has the ability to use a single carbon substrate as its sole source of energy and biomass. $C_1$ metabolizers will typically be methylotrophs and/or methanotrophs.

The term "methylotroph" means an organism capable of oxidizing organic compounds that do not contain carbon-carbon bonds. Where the methylotroph is able to oxidize $CH_4$, the methylotroph is also a methanotroph.

The term "methanotroph" or "methanotrophic bacteria" means a prokaryote capable of utilizing methane as its primary source of carbon and energy. Complete oxidation of methane to carbon dioxide occurs by aerobic degradation pathways. Typical examples of methanotrophs useful in the present invention include (but are not limited to) the genera *Methylomonas*, *Methylobacter*, *Methylococcus*, and *Methylosinus*.

The term "high growth methanotrophic bacterial strain" refers to a bacterium capable of growth with methane or methanol as the sole carbon and energy source and which possesses a functional Embden-Meyerof carbon flux pathway resulting in a high rate of growth and yield of cell mass per gram of $C_1$ substrate metabolized. The specific "high growth methanotrophic bacterial strain" described herein is referred to as "*Methylomonas* 16a", "16a" or "*Methylomonas* sp. 16a", which terms are used interchangeably and which refer to the *Methylomonas* sp. 16a (ATCC PTA-2402) strain (U.S. Pat. No. 6,689,601).

The term "crt gene cluster" in *Methylomonas* refers to an open reading frame comprising crtN1, ald, and crtN2 that is active in the native $C_{30}$ carotenoid biosynthetic pathway of *Methylomonas* sp. 16a.

The term "CrtN1" refers to an enzyme encoded by the crtN1 gene, active in the native carotenoid biosynthetic pathway of *Methylomonas* sp. 16a. This gene is the first gene located on the crt gene cluster in *Methylomonas*.

The term "ALD" refers to an enzyme encoded by the ald gene, active in the native carotenoid biosynthetic pathway of *Methylomonas* sp. 16a. This gene is the second gene located on the crt gene cluster in *Methylomonas*.

The term "CrtN2" refers to an enzyme encoded by the crtN2 gene, active in the native carotenoid biosynthetic pathway of *Methylomonas* sp. 16a. This gene is the third gene located on the crt gene cluster in *Methylomonas*.

The term "CrtN3" refers to an enzyme encoded by the crtN3 gene, which affects the native carotenoid biosynthesis in *Methylomonas* sp. 16a. This gene is not located within the crt gene cluster; instead this gene is present in a different locus within the *Methylomonas* genome (WO 02/18617).

The term "pigmentless" or "white mutant" or "non-pigmented strain" refers to a *Methylomonas* sp. 16a bacterium wherein the native pink pigment (e.g., a $C_{30}$ carotenoid) is not produced. Thus, the bacterial cells appear white in color, as opposed to pink. *Methylomonas* sp. 16a white mutants have been engineered by deleting all or a portion of the native $C_{30}$ carotenoid genes. For example, disruption of either the ald/crtN1 genes or the promoter driving the native crt gene cluster in *Methylomonas* sp. 16a creates a non-pigmented ("white") mutant better suited for $C_{40}$ carotenoid production (WO 02/18617).

The term "*Methylomonas* sp. 16a MWM1000" or "MWM1000" refers to a non-pigmented methanotropic bacterial strain created by deleting a portion of the ald and crtN1 genes native to *Methylomonas* sp. 16a (WO 02/18617). The deletion disrupted $C_{30}$ carotenoid production in MWM1000. The ald/crtN1 deletion is denoted as "Δald/crtN1".

As used herein, an "isolated nucleic acid molecule" is a polymer of RNA or DNA that is single- or double-stranded, optionally containing synthetic, non-natural or altered nucleotide bases. An isolated nucleic acid molecule in the form of a polymer of DNA may be comprised of one or more segments of cDNA, genomic DNA or synthetic DNA.

A nucleic acid molecule is "hybridizable" to another nucleic acid molecule, such as a cDNA, genomic DNA, or RNA molecule, when a single-stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, $2^{nd}$ ed., Cold Spring Harbor Laboratory: Cold Spring Harbor, N.Y. (1989), particularly Chapter 11 and Table 11.1 therein (hereinafter "Maniatis"). The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washed with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridization decreases in the following order: RNA:RNA, DNA:RNA, DNA:DNA. For hybrids of greater than 100 nucleotides in length, equations for calculating Tm have been derived (see Maniatis, supra, 9.50–9.51). For hybridizations with shorter nucleic acids, i.e., oligonucleotides, the position of mismatches becomes more important, and the length of the oligonucleotide determines its specificity (see Maniatis, supra, 11.7–11.8). In one embodiment, the length for a hybridizable nucleic acid is at least about 10 nucleotides. Preferably a minimum length for a hybridizable nucleic acid is at least about 15 nucleotides; more preferably at least about 20 nucleotides; and most preferably the length is at least about 30 nucleotides. Furthermore, the skilled artisan will recognize that the temperature and wash solution salt concentration may be adjusted as necessary according to factors such as length of the probe.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.* 215:403–410 (1993)). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches partial or complete amino acid and nucleotide sequences encoding one or more particular microbial proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable of hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing, as well as those substantially similar nucleic acid sequences.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humana: NJ (1994); 4.) *Sequence Analysis in Molecular Biology* (von Heinje, G., Ed.) Academic (1987); and 5.) *Sequence Analysis Primer*

(Gribskov, M. and Devereux, J., Eds.) Stockton: NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences is performed using the Clustal method of alignment (Higgins and Sharp, *CABIOS.* 5:151–153 (1989)) with default parameters (GAP PENALTY=10, GAP LENGTH PENALTY=10). Default parameters for pairwise alignments using the Clustal method are: KTUPLE 1, GAP PENALTY=3, WINDOW=5 and DIAGONALS SAVED=5.

Suitable nucleic acid fragments (isolated polynucleotides of the present invention) encode polypeptides that are at least about 70% identical, preferably at least about 75% identical, and more preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

"Codon degeneracy" refers to the nature in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the instant microbial polypeptides as set forth in SEQ ID NOs:2, 4, 6, 8, 10, and 12. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments that are then enzymatically assembled to construct the entire gene. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene rmtay comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing sites, effector binding sites and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The "3' non-coding sequences" refer to DNA sequences located downstream of a coding sequence and include polyadenylation recognition sequences and other sequences encoding regulatory signals capable of affecting mRNA processing or gene expression. The polyadenylation signal (normally limited to eukaryotes) is usually characterized by affecting the addition of polyadenylic acid tracts to the 3' end of the mRNA precursor.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA" or "mRNA" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to an RNA transcript that is complementary to all or part of a target primary transcript or mRNA and that blocks the expression of a target gene (U.S. Pat. No. 5,107,065; WO 99/28508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be (but are not limited to) intracellular localization signals.

The term "signal peptide" refers to an amino terminal polypeptide preceding the secreted mature protein. The signal peptide is cleaved from, and is therefore not present in, the mature protein. Signal peptides have the function of directing and translocating secreted proteins across cell membranes. A signal peptide is also referred to as a signal protein.

"Conjugation" refers to a particular type of transformation in which a unidirectional transfer of DNA (e.g., from a bacterial plasmid) occurs from one bacterium cell (i.e., the "donor") to another (i.e., the "recipient"). The process involves direct cell-to-cell contact. Sometimes another bacterial cell (i.e., the "helper") is present to facilitate the conjugation.

"Transformation" refers to the transfer of a nucleic acid fragment into the genome of a host organism, resulting in genetically stable inheritance. Host organisms containing the transformed nucleic acid fragments are referred to as "transgenic", "recombinant" or "transformed" organisms.

The terms "plasmid", "vector" and "cassette" refer to an extra chromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequences into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

The term "altered biological activity" will refer to an activity, associated with a protein encoded by a nucleotide sequence which can be measured by an assay method, where that activity is either greater than or less than the activity associated with the native sequence. "Enhanced biological activity" refers to an altered activity that is greater than that associated with the native sequence. "Diminished biological activity" is an altered activity that is less than that associated with the native sequence.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.* 215: 403–410 (1990)); 3.) DNASTAR (DNASTAR, Inc. Madison, Wis.); 4.) the FASTA program incorporating the Smith-Waterman algorithm (W. R. Pearson, *Comput. Methods Genome Res.*, [Proc. Int. Symp.] (1994), Meeting Date 1992, 111–20. Editor(s): Suhai, Sandor. Plenum: New York, N.Y.); and 5.) the Vector NTI version 7.0 programs (Informax, Inc., Bethesda, Md.). Within the context of this application it will be understood that where sequence analysis software is used for analysis, that the results of the analysis will be based on the "default values" of the program referenced, unless otherwise specified. As used herein "default values" will mean any set of values or parameters (set by the manufacturer) which originally load with the software when first initialized.

Standard recombinant DNA and molecular cloning techniques used herein are well known in the art and are described by Maniatis (supra); by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience (1987).

Genes Involved in Carotenoid Production

The enzyme pathway involved in the biosynthesis of carotenoid compounds can be conveniently viewed in two parts, the upper isoprenoid pathway providing for the conversion of pyruvate and glyceraldehyde-3-phosphate to farnesyl pyrophosphate and the lower carotenoid biosynthetic pathway, which provides for the synthesis of either diapophytoene or phytoene and all subsequently produced carotenoids (FIG. 1). The upper pathway is ubiquitous in many microorganisms and in these cases it will only be necessary to introduce genes that comprise the lower pathway for the biosynthesis of the desired carotenoid. The division between the two pathways concerns the synthesis of farnesyl pyrophosphate (FPP). Where FPP is naturally present, only elements of the lower carotenoid pathway will be needed. However, it will be appreciated that for the lower pathway carotenoid genes to be effective in the production of carotenoids, it will be necessary for the host cell to have suitable levels of FPP within the cell. Where FPP synthesis is not provided by the host cell, it will be necessary to introduce the genes necessary for the production of FPP. Each of these pathways will be discussed below in detail.

The Upper Isoprenoid Pathway

Isoprenoid biosynthesis occurs through either of two pathways, generating the common $C_5$ isoprene subunit, isopentenyl pyrophosphate (IPP). First, IPP may be synthesized through the well-known acetate/mevalonate pathway. However, recent studies have demonstrated that the mevalonate-dependent pathway does not operate in all living organisms. An alternate mevalonate-independent pathway for IPP biosynthesis has been characterized in bacteria and in green algae and higher plants (Horbach et al., *FEMS Microbiol. Lett.* 111:135–140 (1993); Rohmer et al., *Biochem.* 295:517–524 (1993); Schwender et al., *Biochem.* 316:73–80 (1996); Eisenreich et al., *Proc. Natl. Acad. Sci. USA* 93:6431–6436 (1996)).

Many steps in the mevalonate-independent isoprenoid pathway are known (FIG. 1). For example, the initial steps of the alternate pathway leading to the production of IPP have been studied in *Mycobacterium tuberculosis* by Cole et al. (*Nature* 393:537–544 (1998)). The first step of the pathway involves the condensation of two 3-carbon molecules (pyruvate and D-glyceraldehyde 3-phosphate) to yield a 5-carbon compound known as D-1-deoxyxylulose-5-phosphate. This reaction occurs by the Dxs enzyme, encoded by the dxs gene. Next, the isomerization and reduction of D-1-deoxyxylulose-5-phosphate yields 2-C-methyl-D-erythritol-4-phosphate. One of the enzymes involved in the isomerization and reduction process is D-1-deoxyxylulose-5-phosphate reductoisomerase (Dxr), encoded by the gene dxr. 2-C-methyl-D-erythritol-4-phosphate is subsequently converted into 4-diphosphocytidyl-2C-methyl-D-erythritol in a CTP-dependent reaction by the enzyme encoded by the non-annotated gene ygbP (Cole et al., supra). Recently, however, the ygbP gene was renamed as ispD as a part of the isp gene cluster (SwissProtein Accession #Q46893).

Next, the $2^{nd}$ position hydroxy group of 4-diphosphocytidyl-2C-methyl-D-erythritol can be phosphorylated in an ATP-dependent reaction by the enzyme encoded by the ychB gene. This product phosphorylates 4-diphosphocytidyl-2C-methyl-D-erythritol, resulting in 4-diphosphocytidyl-2C-methyl-D-erythritol 2-phosphate. The ychB gene was renamed as ispE, also as a part of the isp gene cluster (SwissProtein Accession #P24209). Finally, the product of the ygbB gene converts 4-diphosphocytidyl-2C-methyl-D-erythritol 2-phosphate to 2C-methyl-D-erythritol 2,4-cyclodiphosphate in a CTP-dependent manner. This gene has also been recently renamed, and belongs to the isp gene cluster. Specifically, the new name for the ygbB gene is ispF (SwissProtein Accession #P36663). The product of the pyrG gene is important in these reactions, as a CTP synthase.

The enzymes encoded by the lytB and gcpE genes (and perhaps others) are thought to participate in the reactions leading to formation of isopentenyl pyrophosphate (IPP) and dimethylallyl pyrophosphate (DMAPP). IPP may be isomerized to DMAPP via IPP isomerase, encoded by the idi gene; however, this enzyme is not essential for survival and may be absent in some bacteria using the 2-C-methyl-D-erythritol 4-phosphate (MEP) pathway. Recent evidence suggests that the MEP pathway branches before IPP and separately produces IPP and DMAPP via the lytB gene product. A lytB knockout mutation is lethal in *E. coli* except in media supplemented with both IPP and DMAPP.

The synthesis of FPP occurs via the isomerization of IPP to dimethylallyl pyrophosphate (DMAPP). This reaction is followed by a sequence of two prenyltransferase reactions catalyzed by ispA, leading to the creation of geranyl pyrophosphate (GPP; a 10-carbon molecule) and farnesyl pyrophosphate (FPP; a 15-carbon molecule); respectively.

The Lower Carotenoid Biosynthetic Pathway

The division between the upper isoprenoid pathway and the lower carotenoid pathway is somewhat subjective. Because FPP synthesis is common in both carotenogenic and non-carotenogenic bacteria, the Applicant considers the first step in the lower carotenoid biosynthetic pathway to begin with the conversion of farnesyl pyrophosphate (FPP) to compounds of two divergent pathways, leading to the formation of either $C_{30}$ diapocarotenoids or $C_{40}$ carotenoids.

Within the $C_{40}$ pathway, the first step in the biosynthetic pathway begins with the prenyltransferase reaction converting farnesyl pyrophosphate (FPP) to a 20-carbon molecule known as geranylgeranyl pyrophosphate (GGPP) by the addition of IPP. The gene crtE (EC 2.5.1.29), encoding GGPP synthetase, is responsible for this prenyltransferase reaction. Then, a condensation reaction of two molecules of GGPP occurs to form phytoene ((7,8,11,12,7',8',11',12'-ω-octahydro-ω, ω-carotene; or PPPP), the first 40-carbon molecule of the lower carotenoid biosynthesis pathway. This enzymatic reaction is catalyzed by CrtB (phytoene synthase; EC 2.5.1.-).

Figure 2:
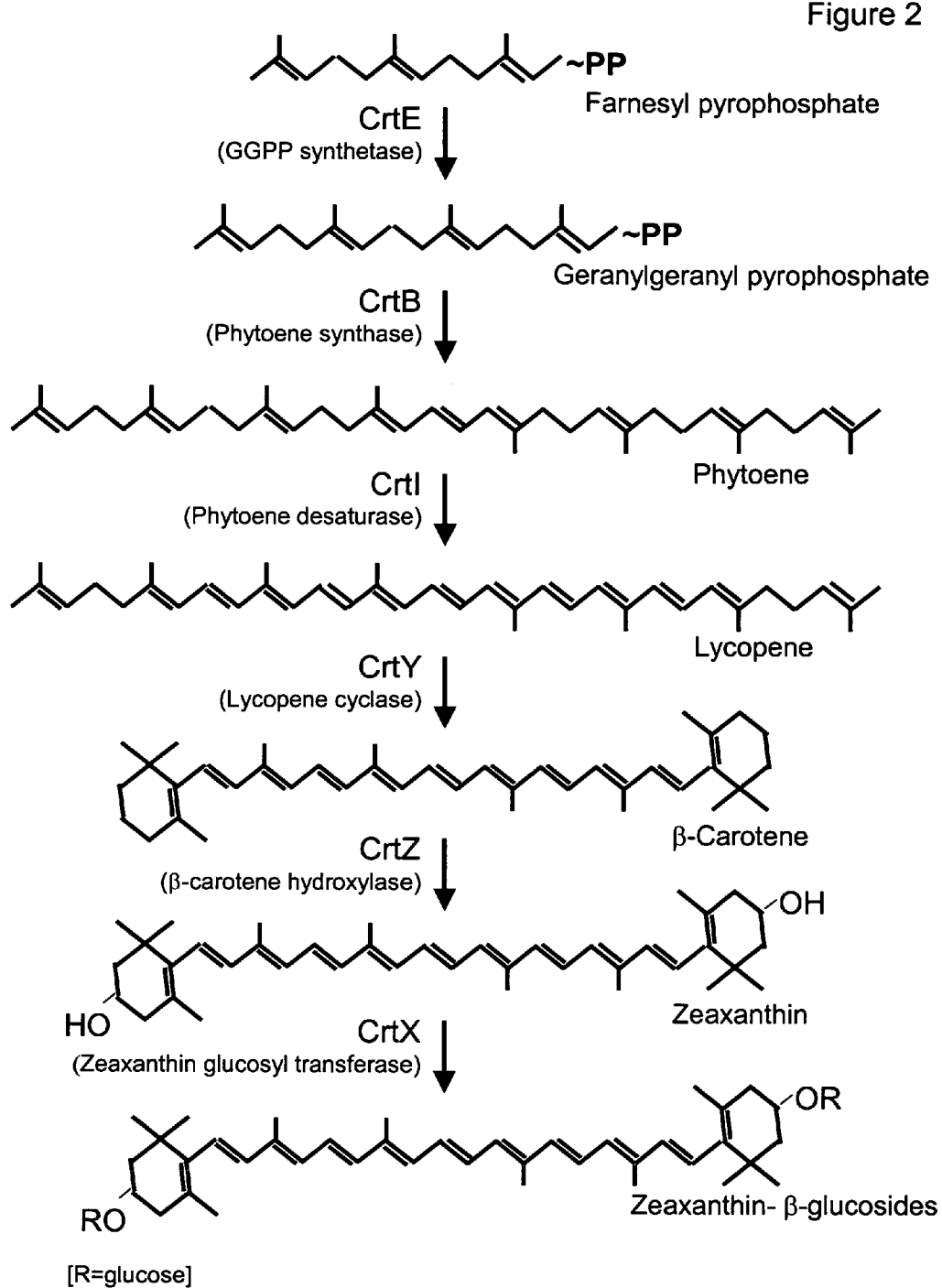
FIG. 2 shows a portion of the lower $C_{40}$ carotenoid biosynthetic pathway, to illustrate the specific chemical conversions catalyzed by CrtE, CrtX, CrtY, CrtI, CrtB, and CrtZ.

From the compound phytoene, a spectrum of $C_{40}$ carotenoids is produced by subsequent hydrogenation, dehydrogenation, cyclization, oxidation, or any combination of these processes. For example, lycopene, which imparts a "red"-colored spectra, is produced from phytoene through four sequential dehydrogenation reactions by the removal of eight atoms of hydrogen, catalyzed by the gene crtI (encoding phytoene desaturase) (see FIG. 2). Lycopene cyclase (CrtY) converts lycopene to β-carotene (β,β-carotene). β-carotene is converted to zeaxanthin ((3R,3'R)-β,β-carotene-3,3'-diol) via a hydroxylation reaction resulting from the activity of β-carotene hydroxylase (encoded by the crtZ gene). Zeaxanthin can be converted to zeaxanthin-β-glucosides by zeaxanthin glucosyl transferase (EC 2.4.1.-; encoded by the crtX gene).

In addition to crtE, crtX, crtY, crtI, crtB, and crtZ, which can be utilized in combination to create phytoene, lycopene, β-carotene, zeaxanthin, and zeaxanthin-β-glucosides, various other crt genes are known which enable the intramolecular conversion of linear $C_{40}$ compounds to produce numerous other functionalized carotenoid compounds. One skilled in the art will be able to identify various other crt genes, according to publicly available literature (e.g., GenBank®), the patent literature, and experimental analysis of microorganisms having the ability to produce carotenoids. For example:

β-carotene can be converted to canthaxanthin by β-carotene ketolases encoded by crtW (e.g., GenBank® Accession #s AF218415, D45881, D58420, D58422, X86782, Y15112), crtO (e.g., GenBank® Accession #s X86782, Y15112) or bkt. Echinenone in an intermediate in this reaction.

Canthaxanthin can be converted to astaxanthin by β-carotene hydroxylase encoded by the crtZ gene. Adonirubin is an intermediate in this reaction.

Zeaxanthin can be converted to astaxanthin by β-carotene ketolases encoded by crtW, crtO, or bkt. Adonixanthin is an intermediate in this reaction.

Spheroidene can be converted to spheroidenone by spheroidene monooxygenase encoded by crtA (e.g., GenBank® Accession #s AJ010302, Z11165, X52291).

Neurosporene can be converted to spheroidene and lycopene can be converted to spirilloxanthin by the sequential actions of hydroxyneurosporene synthase, methoxyneurosporene desaturase and hydroxyneurosporene-O-methyltransferase encoded by the crtC (e.g., GenBank® Accession #s AB034704, AF195122, AJ010302, AF287480, U73944, X52291, Z11165, Z21955), crtD (e.g., GenBank® Accession #s AJ010302, X63204, U73944, X52291, Z11165) and crtF (e.g., GenBank® Accession #s AB034704, AF288602, AJ010302, X52291, Z11165) genes, respectively.

β-carotene can be converted to isorenieratene by β-carotene desaturase encoded by crtU (e.g., GenBank® Accession #s AF047490, AF121947, AF139916, AF195507, AF272737, AF372617, AJ133724, AJ224683, D26095, U38550, X89897, and Y15115).

These examples are not limiting and many other carotenoid genes and products exist within this $C_{40}$ lower carotenoid biosynthetic pathway. Thus, by using various combinations of the crtE, crtX, crtY, crtI, crtB, and crtZ genes presented herein, optionally in addition with any other known crt gene(s) isolated from plant, animal, and/or bacterial sources, innumerable different carotenoids and carotenoid derivatives could be made using the methods of the present invention, provided sufficient sources of FPP are available in the host organism.

It is envisioned that useful products of the present invention will include any carotenoid compound as defined herein including, but not limited to: antheraxanthin, adonirubin, adonixanthin, astaxanthin, canthaxanthin, capsorubrin, β-cryptoxanthin, α-carotene, β-carotene, epsilon-carotene, echinenone, 3-hydroxyechinenone, 3'-hydroxyechinenone, γ-carotene, 4-keto-γ-carotene, ζ-carotene, α-cryptoxanthin, deoxyflexixanthin, diatoxanthin, 7,8-didehydroastaxanthin, fucoxanthin, fucoxanthinol, isorenieratene, lactucaxanthin, lutein, lycopene, myxobactone, neoxanthin, neurosporene, hydroxyneurosporene, peridinin, phytoene, rhodopin, rhodopin glucoside, 4-keto-rubixanthin, siphonaxanthin, spheroidene, spheroidenone, spirilloxanthin, 4-keto-torulene, 3-hydroxy-4-keto-torulene, uriolide, uriolide acetate, violaxanthin, zeaxanthin-β-diglucoside, and zeaxanthin. Additionally, the invention encompasses derivitization of these molecules to create hydroxy-, methoxy-, oxo-, epoxy-, carboxy-, or aldehydic functional groups, or glycoside esters, or sulfates. Sequence Identification of Strain DC260 Carotenoid Biosynthetic Genes and Enzymes A variety of nucleotide sequences have been isolated from strain DC260 encoding gene products involved in the $C_{40}$ lower carotenoid pathway. ORF's 1–6, for example, encode the crtE, crtX, crtY, crtI, crtB and crtZ genes in the lower carotenoid biosynthetic pathway (see FIGS. 1 and 2) and their enzymatic products lead to the production of the pigmented carotenoids lycopene, β-carotene, zeaxanthin, and zeaxanthin-β-glucosides.

The entire set of genes (crtE, crtX, crtY, crtI, crtB and crtZ) isolated from strain DC260 are disclosed herein in a single sequence (SEQ ID NO:18). This gene cluster has been placed on a vector and expressed in microbial hosts for the production of carotenoid compounds. The skilled person will recognize that minor nucleic acid substitutions, additions and deletions (such as the substitutions of preferred codons for specific host cell expression) may be made to such a gene cluster without affecting its utility provided that all of the encoded polypeptides are expressed and are enzymatically active. Accordingly it is within the scope of the invention to provide an isolated nucleic acid molecule as set forth in SEQ ID NO:18, comprising the crtE, crtX, crtY, crtI, crtB and crtZ, genes or an isolated nucleic acid molecule having at least 95% identity to SEQ ID NO:18, wherein the isolated nucleic acid molecule encodes all of the polypeptides crtE, crtX, crtY, crtI, crtB and crtZ.

Comparison of the crtE nucleotide base and deduced amino acid sequences (ORF 1) to public databases reveals that the most similar known sequences are about 54% identical to the amino acid sequence of CrtE reported herein over a length of 301 amino acids using a Smith-Waterman alignment algorithm (W. R. Pearson, supra). More preferred amino acid fragments are at least about 70%–80% identical to the sequences herein, where those sequences that are 85%–90% identical are particularly suitable and those sequences that are about 95% identical are most preferred. Similarly, preferred crtE encoding nucleic acid sequences corresponding to the instant ORF's are those encoding active proteins and which are at least about 70%–80% identical to the nucleic acid sequences of crtE reported herein, where those sequences that are 85%–90% identical are particularly suitable and those sequences that are about 95% identical are most preferred.

Comparison of the crtX nucleotide base and deduced amino acid sequences (ORF 2) to public databases reveals that the most similar known sequences are about 52% identical to the amino acid sequence of CrtX reported herein over a length of 425 amino acids using a Smith-Waterman alignment algorithm (W. R. Pearson, supra). More preferred amino acid fragments are at least about 70%–80% identical to the sequences herein, where those sequences that are 85%–90% identical are particularly suitable and those sequences that are about 95% identical are most preferred. Similarly, preferred crtX encoding nucleic acid sequences corresponding to the instant ORF's are those encoding active proteins and which are at least about 70%–80% identical to the nucleic acid sequences of crtX reported herein, where those sequences that are 85%–90% identical are particularly suitable and those sequences that are about 95% identical are most preferred.

Comparison of the crtY nucleotide base and deduced amino acid sequences (ORF 3) to public databases reveals that the most similar known sequences are about 53% identical to the amino acid sequence of CrtY reported herein over a length of 388 amino acids using a Smith-Waterman alignment algorithm (W. R. Pearson, supra). More preferred amino acid fragments are at least about 70%–80% identical to the sequences herein, where those sequences that are 85%–90% identical are particularly suitable and those sequences that are about 95% identical are most preferred. Similarly, preferred crtY encoding nucleic acid sequences corresponding to the instant ORF's are those encoding active proteins and which are at least about 70%–80% identical to the nucleic acid sequences of crtY reported herein, where those sequences that are 85%–90% identical are particularly suitable and those sequences that are about 95% identical are most preferred.

Comparison of the crtI nucleotide base and deduced amino acid sequences (ORF 4) to public databases reveals that the most similar known sequences are about 77% identical to the amino acid sequence of CrtI reported herein over a length of 493 amino acids using a Smith-Waterman alignment algorithm (W. R. Pearson, supra). More preferred amino acid fragments are at least about 70%–80% identical to the sequences herein, where those sequences that are 85%–90% identical are particularly suitable and those sequences that are about 95% identical are most preferred. Similarly, preferred crtI encoding nucleic acid sequences corresponding to the instant ORF's are those encoding active proteins and which are at least about 70%–80% identical to the nucleic acid sequences of crtI reported herein, where those sequences that are 85%–90% identical are particularly suitable and those sequences that are about 95% identical are most preferred.

Comparison of the crtB nucleotide base and deduced amino acid sequences (ORF 5) to public databases reveals that the most similar known sequences are about 60% identical to the amino acid sequence of CrtB reported herein over a length of 309 amino acids using a Smith-Waterman alignment algorithm (W. R. Pearson, supra). More preferred amino acid fragments are at least about 70%–80% identical to the sequences herein, where those sequences that are 85%–90% identical are particularly suitable and those sequences that are about 95% identical are most preferred. Similarly, preferred crtB encoding nucleic acid sequences corresponding to the instant ORF's are those encoding active proteins and which are at least about 70%–80% identical to the nucleic acid sequences of crtB reported herein, where those sequences that are 85%–90% identical are particularly suitable and those sequences that are about 95% identical are most preferred.

Comparison of the crtZ nucleotide base and deduced amino acid sequences (ORF 6) to public databases reveals that the most similar known sequences are about 66% identical to the amino acid sequence of CrtZ reported herein over a length of 177 amino acids using a Smith-Waterman alignment algorithm (W. R. Pearson, supra). More preferred amino acid fragments are at least about 70%–80% identical to the sequences herein, where those sequences that are 85%–90% identical are particularly suitable and those sequences that are about 95% identical are most preferred. Similarly, preferred crtZ encoding nucleic acid sequences corresponding to the instant ORF's are those encoding active proteins and which are at least about 70%–80% identical to the nucleic acid sequences of crtZ reported herein, where those sequences that are 85%–90% identical are particularly suitable and those sequences that are about 95% identical are most preferred.

Isolation of Homologs

Each of the nucleic acid fragments of the $C_{40}$ lower carotenoid biosynthetic pathway of the instant invention may be used to isolate genes encoding homologous proteins from the same or other microbial (or plant) species. Isolation of homologous genes using sequence-dependent protocols is well known in the art. Examples of sequence-dependent protocols include, but are not limited to: 1.) methods of nucleic acid hybridization; 2.) methods of DNA and RNA amplification, as exemplified by various uses of nucleic acid amplification technologies [e.g., polymerase chain reaction (PCR), Mullis et al., U.S. Pat. No. 4,683,202; ligase chain reaction (LCR), Tabor, S. et al., *Proc. Natl. Acad. Sci. USA* 82:1074 (1985); or strand displacement amplification (SDA), Walker, et al., *Proc. Natl. Acad. Sci. USA,* 89:392 (1992)]; and 3.) methods of library construction and screening by complementation.

For example, genes encoding similar proteins or polypeptides to those of the $C_{40}$ lower carotenoid biosynthetic pathway, as described herein, could be isolated directly by using all or a portion of the instant nucleic acid fragments as DNA hybridization probes to screen libraries from any desired bacteria using methodology well known to those skilled in the art (wherein those bacteria producing $C_{40}$ carotenoids would be preferred). Specific oligonucleotide probes based upon the instant nucleic acid sequences can be designed and synthesized by methods known in the art (Maniatis, supra). Moreover, the entire sequences can be used directly to synthesize DNA probes by methods known to the skilled artisan (e.g., random primers DNA labeling, nick translation, or end-labeling techniques), or RNA probes using available in vitro transcription systems. In addition, specific primers can be designed and used to amplify a part of (or full-length of) the instant sequences. The resulting amplification products can be labeled directly during amplification reactions or labeled after amplification reactions, and used as probes to isolate full-length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotide as specific hybridization probes in the Diagnosis of Genetic Disorders", in *Human Genetic Diseases: A Practical Approach*, K. E. Davis Ed., (1986) pp 33–50, IRL: Herndon, V A; and Rychlik, W., In *Methods in Molecular Biology*, White, B. A. (Ed.), (1993) Vol. 15, pp 31–39, PCR Protocols: Current Methods and Applications. Humania: Totowa, N.J.).

Generally two short segments of the instant sequences may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding microbial genes.

Alternatively, the second primer sequence may be based upon sequences derived from the cloning vector. For example, the skilled artisan can follow the RACE protocol (Frohman et al., *Proc. Natl. Acad. Sci. USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL, Gaithersburg, Md.), specific 3' or 5' cDNA fragments can be isolated (Ohara et al., *Proc. Natl. Acad. Sci. USA* 86:5673 (1989); Loh et al., *Science* 243:217 (1989)).

Alternatively, the instant sequences of the $C_{40}$ lower carotenoid biosynthetic pathway may be employed as hybridization reagents for the identification of homologs. The basic components of a nucleic acid hybridization test include a probe, a sample suspected of containing the gene or gene fragment of interest, and a specific hybridization method. Probes of the present invention are typically single-stranded nucleic acid sequences that are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions which will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed. Optionally, a chaotropic agent may be added. The chaotropic agent stabilizes nucleic acids by inhibiting nuclease activity. Furthermore, the chaotropic agent allows sensitive and stringent hybridization of short oligonucleotide probes at room temperature (Van Ness and Chen, *Nucl. Acids Res.* 19:5143–5151 (1991)). Suitable chaotropic agents include guanidinium chloride, guanidinium thiocyanate, sodium thiocyanate, lithium tetrachloroacetate, sodium perchlorate, rubidium tetrachloroacetate, potassium iodide, and cesium trifluoroacetate, among others. Typically, the chaotropic agent will be present at a final concentration of about 3 M. If desired, one can add formamide to the hybridization mixture, typically 30–50% (v/v).

Various hybridization solutions can be employed. Typically, these comprise from about 20 to 60% volume, preferably 30%, of a polar organic solvent. A common hybridization solution employs about 30–50% v/v formamide, about 0.15 to 1 M sodium chloride, about 0.05 to 0.1 M buffers (e.g., sodium citrate, Tris-HCl, PIPES or HEPES (pH range about 6–9)), about 0.05 to 0.2% detergent (e.g., sodium dodecylsulfate), or between 0.5–20 mM EDTA, FICOLL (Pharmacia Inc.) (about 300–500 kdal), polyvinylpyrrolidone (about 250–500 kdal), and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol glycine. Other additives may also be included, such as volume exclusion agents that include a variety of polar water-soluble or swellable agents (e.g., polyethylene glycol), anionic polymers (e.g., polyacrylate or polymethylacrylate), and anionic saccharidic polymers (e.g., dextran sulfate).

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

Availability of the instant nucleotide and deduced amino acid sequences facilitates immunological screening of DNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen DNA expression libraries to isolate full-length DNA clones of interest (Lerner, R. A., *Adv. Immunol.* 36:1 (1984); Maniatis, supra).

Recombinant Expression in Microorganisms

The genes and gene products of the instant sequences may be produced in heterologous host cells, particularly in the cells of microbial hosts. Expression in recombinant microbial hosts may be useful for the expression of various pathway intermediates, and/or for the modulation of pathways already existing in the host for the synthesis of new products heretofore not possible using the host.

Methods for introduction of genes encoding the appropriate upper isoprene pathway genes and various combinations of the lower carotenoid biosynthetic pathway genes of the instant invention (optionally with other crt genes) into a suitable microbial host are common. As will be obvious to one skilled in the art, the particular functionalities required to be introduced into a host organism for production of a particular carotenoid product will depend on the host cell (and its native production of isoprenoid compounds), the availability of substrate, and the desired end product(s).

It will be appreciated that for the present crt genes to be effective in the production of carotenoids, it will be necessary for the host cell to have suitable levels of FPP within the cell. FPP may be supplied exogenously, or may be produced endogenously by the cell, either through native or introduced genetic pathways. It is contemplated, therefore, that where a specific host cell does not have the genetic machinery to produce suitable levels of FPP, it is well within the grasp of the skilled person in the art to obtain any necessary genes of the upper isoprenoid pathway and engineer these genes into the host to produce FPP as the starting material for carotenoid biosynthesis. As a precursor of FPP, IPP may be synthesized through the well-known acetate/mevalonate pathway. Alternatively, recent studies have demonstrated that the mevalonate-dependent pathway does not operate in all living organisms; an alternate mevalonate-independent pathway for IPP biosynthesis has been characterized in bacteria and in green algae and higher plants (Horbach et al., *FEMS Microbiol. Lett.* 111:135–140 (1993); Rohmer et al, *Biochem.* 295: 517–524 (1993); Schwender et al., *Biochem.* 316: 73–80 (1996); Eisenreich et al., *Proc. Natl. Acad. Sci. USA* 93: 6431–6436 (1996)).

It is expected, for example, that introduction of chimeric genes encoding one or more of the instant lower $C_{40}$ carotenoid biosynthetic pathway crtEXYIBZ sequences will lead to production of carotenoid compounds in the host microbe of choice. With an appropriate genetic transformation system, it should be possible to genetically engineer a variety of non-carotenogenic hosts. This has been shown, for example, using *Erwinia herbicola* crt genes, to produce various carotenoids in the hosts *E. coli, Agrobacterium tumefaciens, Saccharomyces cerevisiae, Pichia pastoris* (yeast), *Aspergillus nidulans* (fungi), *Rhodobacter sphaeroides*, and higher plants (U.S. Pat. No. 5,656,472). Thus, as described previously herein, antheraxanthin, adonirubin, adonixanthin, astaxanthin, canthaxanthin, capsorubrin, β-cryptoxanthin, α-carotene, β-carotene, epsilon-carotene, echinenone, 3-hydroxyechinenone, 3'-hydroxyechinenone, γ-carotene, 4-keto-γ-carotene, ζ-carotene, α-cryptoxanthin, deoxyflexixanthin, diatoxanthin, 7,8-didehydroastaxanthin, fucoxanthin, fucoxanthinol, isorenieratene, lactucaxanthin, lutein, lycopene, myxobactone, neoxanthin, neurosporene, hydroxyneurosporene, peridinin, phytoene, rhodopin, rhodopin glucoside, 4-keto-rubixanthin, siphonaxanthin, spheroidene, spheroidenone, spirilloxanthin, 4-keto-torulene, 3-hydroxy-4-keto-torulene, uriolide, uriolide acetate, violaxanthin, zeaxanthin-β-diglucoside, and zeaxanthin may all be produced in microbial hosts using the teachings herein, by introducing various combinations of the following crt enzyme functionalities (for example): CrtE, CrtX, CrtY, CrtI, CrtB, CrtZ, CrtW, CrtO, CrtA, CrtC, CrtD, CrtF, and CrtU. Thus, formation of phytoene from FPP requires CrtE and CrtB; the carotenoid-specific genes necessary for the synthesis of lycopene from FPP include crtE, crtB and crtI; and genes required for β-carotene production from FPP include crtE, crtB, crtI, and crtY. Given this understanding of the relationship between the crt genes, it will be possible to select appropriate microbial host cells and crt genes for expression of any desired carotenoid product.

Microbial expression systems and expression vectors containing regulatory sequences that direct high level expression of foreign proteins are well known to those skilled in the art. Any of these could be used to construct chimeric genes for production of any of the gene products of the instant sequences. These chimeric genes could then be introduced into appropriate microorganisms via transformation to provide high level expression of the enzymes.

Vectors or cassettes useful for the transformation of suitable host cells are well known in the art. Typically the vector or cassette contains sequences directing transcription and translation of the relevant gene(s), a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Initiation control regions or promoters which are useful to drive expression of the instant ORF's in the desired host cell are numerous and familiar to those skilled in the art. Virtually any promoter capable of driving these genes is suitable for the present invention including, but not limited to: CYC1, HIS3, GAL1, GAL10, ADH1, PGK, PHO5, GAPDH, ADC1, TRP1, URA3, LEU2, ENO, TPI (e.g., useful for expression in *Saccharomyces*); AOX1 (e.g., useful for expression in *Pichia*); and lac, ara, tet, trp, $IP_L$, $IP_R$, T7, tac, and trc (e.g., useful for expression in *Escherichia coli*) as well as the amy, apr, npr promoters and various phage promoters useful for expression in, e.g., *Bacillus*. Additionally, the deoxy-xylulose phosphate synthase or methanol dehydrogenase operon promoter (Springer et al., *FEMS Microbiol Lett* 160:119–124 (1998)), the promoter for polyhydroxyalkanoic acid synthesis (Foellner et al., *Appl. Microbiol. Biotechnol.* 40:284–291 (1993)), promoters identified from native plasmids in methylotrophs (EP 296484), Plac (Toyama et al., *Microbiology* 143:595–602 (1997); EP 62971), Ptrc (Brosius et al., *Gene* 27:161–172 (1984)), promoters identified from methanotrophs (PCT/US03/33698), and promoters associated with antibiotic resistance [e.g., kanamycin (Springer et al., supra; Ueda et al., *Appl. Environ. Microbiol.* 57:924–926 (1991)) or tetracycline (U.S. Pat. No. 4,824,786)] are suitable for expression in C1 metabolizers.

It is necessary to include an artificial ribosomal binding site ("RBS") upstream of a gene to be expressed, when the RBS is not provided by the vector. This is frequently required for the second, third, etc. gene(s) of an operon to be expressed, when a single promoter is driving the expression of a first, second, third, etc. group of genes. Methodology to determine the preferred sequence of a RBS in a particular host organism will be familiar to one of skill in the art, as are means for creation of this synthetic site.

Termination control regions may also be derived from various genes native to the preferred hosts. Optionally, a termination site may be unnecessary; however, it is most preferred if included.

Merely inserting a gene into a cloning vector does not ensure that it will be successfully expressed at the level needed. In response to the need for a high expression rate, many specialized expression vectors have been created by manipulating a number of different genetic elements that control aspects of transcription, translation, protein stability, oxygen limitation, and secretion from the host cell. More specifically, the molecular features that have been manipulated to control gene expression include: 1.) the nature of the relevant transcriptional promoter and terminator sequences; 2.) the strength of the ribosome binding site; 3.) the number of copies of the cloned gene and whether the gene is plasmid-borne or integrated into the genome of the host cell; 4.) the final cellular location of the synthesized foreign protein; 5.) the efficiency of translation in the host organism; 6.) the intrinsic stability of the cloned gene protein within the host cell; and 7.) the codon usage within the cloned gene, such that its frequency approaches the frequency of preferred codon usage of the host cell. Each of these types of modifications are encompassed in the present invention, as means to further optimize expression of $C_{40}$ carotenoids.

Finally, to promote accumulation of $C_{40}$ carotenoids, it may be necessary to reduce or eliminate the expression of certain genes in the target pathway or in competing pathways that may serve as sinks for energy or carbon. Alternatively, it may be useful to over-express various genes upstream of desired carotenoid intermediates to enhance production. Methods of manipulating genetic pathways for the purposes described above are common and well known in the art.

For example, once a key genetic pathway has been identified and sequenced, specific genes may be up-regulated to increase the output of the pathway. For example, additional copies of the targeted genes may be introduced into the host cell on multicopy plasmids such as pBR322. Alternatively the target genes may be modified so as to be under the control of non-native promoters. Where it is desired that a pathway operate at a particular point in a cell cycle or during a fermentation run, regulated or inducible promoters may used to replace the native promoter of the target gene. Similarly, in some cases the native or endogenous promoter may be modified to increase gene expression. For example, endogenous promoters can be altered in vivo by mutation, deletion, and/or substitution (U.S. Pat. No. 5,565,350; Zarling et al., PCT/US93/03868).

Alternatively, where the sequence of the gene to be disrupted is known, one of the most effective methods for gene down-regulation is targeted gene disruption, where foreign DNA is inserted into a structural gene so as to disrupt transcription. This can be effected by the creation of genetic cassettes comprising the DNA to be inserted (often a genetic marker) flanked by sequences having a high degree of homology to a portion of the gene to be disrupted. Introduction of the cassette into the host cell results in insertion of the foreign DNA into the structural gene via the native DNA replication mechanisms of the cell. (See for example Hamilton et al., *J. Bacteriol.* 171:4617–4622 (1989); Balbas et al., *Gene* 136:211–213 (1993); Gueldener et al., *Nucleic Acids Res.* 24:2519–2524 (1996); and Smith et al., *Methods Mol. Cell. Biol.* 5:270–277(1996)).

Antisense technology is another method of down-regulating genes where the sequence of the target gene is known. To accomplish this, a nucleic acid segment from the desired gene is cloned and operably linked to a promoter such that the anti-sense strand of RNA will be transcribed. This construct is then introduced into the host cell and the antisense strand of RNA is produced. Antisense RNA inhibits gene expression by preventing the accumulation of mRNA encoding the protein of interest. The person skilled in the art will know that special considerations are associated with the use of antisense technologies in order to reduce expression of particular genes. For example, the proper level of expression of antisense genes may require the use of different chimeric genes utilizing different regulatory elements known to the skilled artisan.

Although targeted gene disruption and antisense technology offer effective means of down-regulating genes where the sequence is known, other less specific methodologies have been developed that are not sequence-based. For example, cells may be exposed to UV radiation and then screened for the desired phenotype. Mutagenesis with chemical agents is also effective for generating mutants and commonly used substances include chemicals that affect nonreplicating DNA (e.g., $HNO_2$ and $NH_2OH$), as well as agents that affect replicating DNA (e.g., acridine dyes, notable for causing frameshift mutations). Specific methods for creating mutants using radiation or chemical agents are well documented in the art. See, for example: Thomas D. Brock in *Biotechnology: A Textbook of Industrial Microbiology*, $2^{nd}$ ed., (1989) Sinauer Associates: Sunderland, Mass.; or Deshpande, Mukund V., *Appl. Biochem. Biotechnol.* 36: 227–234 (1992).

Another non-specific method of gene disruption is the use of transposable elements or transposons. Transposons are genetic elements that insert randomly in DNA but can be later retrieved on the basis of sequence to determine where the insertion has occurred. Both in vivo and in vitro transposition methods are known. Both methods involve the use of a transposable element in combination with a transposase enzyme. When the transposable element or transposon is contacted with a nucleic acid fragment in the presence of the transposase, the transposable element will randomly insert into the nucleic acid fragment. The technique is useful for random mutagenesis and for gene isolation, since the disrupted gene may be identified on the basis of the sequence of the transposable element. Kits for in vitro transposition are commercially available (see, for example: The Primer Island Transposition Kit, available from Perkin Elmer Applied Biosystems, Branchburg, N.J., based upon the yeast Ty1 element; The Genome Priming System, available from New England Biolabs, Beverly, Mass., based upon the bacterial transposon Tn7; and the EZ::TN Transposon Insertion Systems, available from Epicentre Technologies, Madison, Wis., based upon the Tn5 bacterial transposable element).

Within the context of the present invention, it may be useful to modulate the expression of the carotenoid biosynthetic pathway by any one of the methods described above. For example, the present invention provides a number of isolated genes (i.e., the crtE, crtX, crtY, crtI, crtB and crtZ genes) encoding enzymes in the carotenoid pathway and methods leading to the production of $C_{40}$ carotenoids. Thus, in addition to over-expressing various combinations of the crtE, crtX, crtY, crtI, crtB, and crtZ genes herein to promote increased production of $C_{40}$ carotenoids, it may also be useful to up-regulate the initial condensation of 3-carbon compounds (pyruvate and D-glyceraldehyde 3-phosphate) to increase the yield of the 5-carbon compound D-1-deoxyxylulose-5-phosphate (mediated by the dxs gene). This would increase the flux of carbon entering the carotenoid biosynthetic pathway and permit increased production of $C_{40}$ carotenoids. Alternatively (or in addition to), it may be desirable to knockout the crtM/crtN genes leading to the synthesis of $C_{30}$ carotenoids, if the microbial host is capable of synthesizing these types of compounds. Or, in systems having native functional crtE, crtX, crtY, crtI, crtB, and crtZ genes, the accumulation of β-carotene or zeaxanthin may be effected by the disruption of down-stream genes (e.g., crtZ or crtX) by any one of the methods described above.

Preferred Microbial Hosts

Preferred heterologous host cells for expression of the instant genes and nucleic acid fragments of the lower carotenoid biosynthetic pathway are microbial hosts that can be found broadly within the fungal or bacterial families and which grow over a wide range of temperature, pH values, and solvent tolerances. For example, it is contemplated that any bacteria, yeast, and filamentous fungi will be suitable hosts for expression of the present nucleic acid fragments. Because transcription, translation and the protein biosynthetic apparatus are the same irrespective of the cellular feedstock, functional genes are expressed irrespective of carbon feedstock used to generate cellular biomass. Large-scale microbial growth and functional gene expression may utilize a wide range of simple or complex carbohydrates, organic acids and alcohols, and/or saturated hydrocarbons (e.g., methane or carbon dioxide, in the case of photosynthetic or chemoautotrophic hosts). However, the functional genes may be regulated, repressed or depressed by specific growth conditions, which may include the form and amount of nitrogen, phosphorous, sulfur, oxygen, carbon or any trace micronutrient including small inorganic ions. In addition, the regulation of functional genes may be achieved by the presence or absence of specific regulatory molecules that are added to the culture and are not typically considered nutrient or energy sources. Growth rate may also be an important regulatory factor in gene expression.

Examples of suitable host strains include, but are not limited to: fungal or yeast species such as *Aspergillus, Trichoderma, Saccharomyces, Pichia, Candida, Hansenula, Yarrowia, Rhodosporidium, Lipomyces, Salmonella, Bacillus, Acinetobacter, Zymomonas, Agrobacterium, Flavobacterium, Rhodobacter, Rhodococcus, Streptomyces, Brevibacterium, Corynebacteria, Mycobacterium, Escherichia, Pantoea, Pseudomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella, Methylophilus, Methylobacillus, Methylobacterium, Hyphomicrobium, Xanthobacter, Paracoccus, Nocardia, Arthrobacter, Rhodopseudomonas, Torulopsis, Phaffia*, and *Rhodotorula*.

Methylotrophs and *Methylomonas* sp. 16a as Microbial Hosts

Although a number of carotenoids have been produced from recombinant microbial sources [e.g., *E. coli* and *Candida utilis* for production of lycopene (Farmer, W. R. and Liao, J. C., *Biotechnol. Prog.* 17: 57–61 (2001); Wang et al., *Biotechnol Prog.* 16: 922–926 (2000); Misawa, N. and Shimada, H., *J. Biotechnol.* 59: 169–181 (1998); Shimada et al., *Appl. Environm. Microbiol.* 64:2676–2680 (1998)]; *E. coli, Candida utilis* and *Pfaffia rhodozyma* for production of β-carotene (Albrecht et al., *Biotechnol. Lett.* 21: 791–795 (1999); Miura et al., *Appl. Environm. Microbiol.* 64:1226–1229 (1998); U.S. Pat. No. 5,691,190); *E. coli* and *Candida utilis* for production of zeaxanthin (Albrecht et al., supra; Miura et al., supra; *E. coli* and *Pfaffia rhodozyma* for production of astaxanthin (U.S. Pat. No. 5,466,599; U.S. Pat. No. 6,015,684; U.S. Pat. No. 5,182,208; U.S. Pat. No. 5,972,642); see also: U.S. Pat. No. 5,656,472, U.S. Pat. No. 5,545,816, U.S. Pat. No. 5,530,189, U.S. Pat. No. 5,530,188, U.S. Pat. No. 5,429,939, and U.S. Pat. No. 6,124,113), these methods of producing carotenoids using various combinations of different crt genes suffer from low yields and reliance on relatively expensive feedstocks. Thus, it would be desirable to identify a method that produces higher yields of carotenoids in a microbial host from an inexpensive feedstock.

There are a number of microorganisms that utilize single carbon substrates as their sole energy source. Such microorganisms are referred to herein as "C1 metabolizers". These organisms are characterized by the ability to use carbon substrates lacking carbon to carbon bonds as a sole source of energy and biomass. These carbon substrates include, but are not limited to: methane, methanol, formate, formaldehyde, formic acid, methylated amines (e.g., mono-, di- and tri-methyl amine), methylated thiols, carbon dioxide, and various other reduced carbon compounds which lack any carbon-carbon bonds.

All C1 metabolizing microorganisms are generally classified as methylotrophs. Methylotrophs may be defined as any organism capable of oxidizing organic compounds that do not contain carbon-carbon bonds. However, facultative methylotrophs, obligate methylotrophs, and obligate methanotrophs are all various subsets of methylotrophs. Specifically:

Facultative methylotrophs have the ability to oxidize organic compounds which do not contain carbon-carbon bonds, but may also use other carbon substrates such as sugars and complex carbohydrates for energy and biomass. Facultative methylotrophic bacteria are found in many environments, but are isolated most commonly from soil, landfill and waste treatment sites. Many facultative methylotrophs are members of the β and γ subgroups of the Proteobacteria (Hanson et al., *Microb. Growth C1 Compounds.*, [Int. Symp.], $7^{th}$ (1993), pp 285–302. Murrell, J. Collin and Don P. Kelly, eds. Intercept: Andover, UK; Madigan et al., *Brock Biology of Microorganisms*, $8^{th}$ ed., Prentice Hall: Upper Saddle River, N.J. (1997)).

Obligate methylotrophs are those organisms that are limited to the use of organic compounds that do not contain carbon-carbon bonds for the generation of energy.

Obligate methanotrophs are those obligate methylotrophs that have the distinct ability to oxidize methane.

Additionally, the ability to utilize single carbon substrates is not limited to bacteria but extends also to yeasts and fungi. A number of yeast genera are able to use single carbon substrates as energy sources in addition to more complex materials (i.e., the methylotrophic yeasts).

Although a large number of these methylotrophic organisms are known, few of these microbes have been successfully harnessed in industrial processes for the synthesis of materials. And, although single carbon substrates are cost-effective energy sources, difficulty in genetic manipulation of these microorganisms as well as a dearth of information about their genetic machinery has limited their use primarily to the synthesis of native products.

Despite these hardships, many methanotrophs contain an inherent isoprenoid pathway which enables these organisms to synthesize pigments and provides the potential for one to envision engineering these microorganisms for production of other non-endogenous isoprenoid compounds. Since methanotrophs can use single carbon substrates (i.e., methane or methanol) as an energy source, it could be possible to produce carotenoids at low cost in these organisms. One such example wherein a methanotroph is engineered for production of β-carotene is described in WO 02/18617.

In the present invention, methods are provided for the expression of genes involved in the biosynthesis of carotenoid compounds in microorganisms that are able to use single carbon substrates as a sole energy source. The host microorganism may be any C1 metabolizer that has the ability to synthesize farnesyl pyrophosphate (FPP) as a metabolic precursor for carotenoids. More specifically, facultative methylotrophic bacteria suitable in the present invention include, but are not limited to: *Methylophilus, Methylobacillus, Methylobacterium, Hyphomicrobium, Xanthobacter, Bacillus, Paracoccus, Nocardia, Arthrobacter, Rhodopseudomonas*, and *Pseudomonas*. Specific methylotrophic yeasts useful in the present invention include, but are not limited to: *Candida, Hansenula, Pichia, Torulopsis*, and *Rhodotorula*. And, exemplary methanotrophs are included in, but not limited to, the genera *Methylomonas, Methylobacter, Methylococcus, Methylosinus, Methylocyctis, Methylomicrobium*, and *Methanomonas*.

Of particular interest in the present invention are high growth obligate methanotrophs having an energetically favorable carbon flux pathway. For example, Applicants have discovered a specific strain of methanotroph having several pathway features that makes it particularly useful for carbon flux manipulation. This strain is known as *Methylomonas* sp. 16a (ATCC PTA 2402) (U.S. Pat. No. 6,689,601); and, this particular strain and other related methylotrophs are preferred microbial hosts for expression of the gene products of this invention, useful for the production of $C_{40}$ carotenoids (WO 02/18617).

*Methylomonas* sp. 16a naturally produces $C_{30}$ carotenoids. Odom et al. has reported that expression of $C_{40}$ carotenoid genes in *Methylomonas* 16a produced a mixture of $C_{30}$ and $C_{40}$ carotenoids (WO 02/18617). Several of the genes involved in $C_{30}$ carotenoid production in this strain have been identified including (but not limited to) the crtN1, ald, crtN2, and crtN3 genes. Disruption of the crtN1ald genes or the promoter driving expression of the crtN1/ald/crtN2 gene cluster created various non-pigmented mutants ("white mutants") more suitable for $C_{40}$ carotenoid production (U.S. Ser. No. 60/527,083, hereby incorporated by reference). For example, non-pigmented *Methylomonas* sp. 16a strain MWM1000 was created by disrupting the ald and crtN1 genes.

The *Methylomonas* sp. 16a strain contains several anomalies in the carbon utilization pathway. For example, based on genome sequence data, the strain is shown to contain genes for two pathways of hexose metabolism. The Entner-Douderoff Pathway (which utilizes the keto-deoxy phosphogluconate aldolase enzyme) is present in the strain. It is generally well accepted that this is the operative pathway in obligate methanotrophs. Also present, however, is the Embden-Meyerhof Pathway (which utilizes the fructose bisphosphate aldolase enzyme). It is well known that this pathway is either not present, or not operative, in obligate methanotrophs. Energetically, the latter pathway is most favorable and allows greater yield of biologically useful energy, ultimately resulting in greater yield production of cell mass and other cell mass-dependent products in *Methylomonas* 16a. The activity of this pathway in the *Methylomonas* sp. 16a strain has been confirmed through microarray data and biochemical evidence measuring the reduction of ATP. Although the *Methylomonas* sp. 16a strain has been shown to possess both the Embden-Meyerhof and the Entner- Douderoff pathway enzymes, the data suggests that the Embden-Meyerhof pathway enzymes are more strongly expressed than the Entner-Douderoff pathway enzymes. This result is surprising and counter to existing beliefs concerning the glycolytic metabolism of methanotrophic bacteria. Applicants have discovered other methanotrophic bacteria having this characteristic, including for example, *Methylomonas clara* and *Methylosinus sporium*. It is likely that this activity has remained undiscovered in methanotrophs due to the lack of activity of the enzyme with ATP, the typical phosphoryl donor for the enzyme in most bacterial systems.

A particularly novel and useful feature of the Embden-Meyerhof pathway in strain *Methylomonas* sp. 16a is that the key phosphofructokinase step is pyrophosphate-dependent instead of ATP-dependent. This feature adds to the energy yield of the pathway by using pyrophosphate instead of ATP.

In methanotrophic bacteria, methane is converted to biomolecules via a cyclic set of reactions known as the ribulose monophosphate pathway or RuMP cycle. This pathway is comprised of three phases, each phase being a series of enzymatic steps. The first step is "fixation" or incorporation of C-1 (formaldehyde) into a pentose to form a hexose or six-carbon sugar. This occurs via a condensation reaction between a 5-carbon sugar (pentose) and formaldehyde and is catalyzed by hexulose monophosphate synthase. The second phase is termed "cleavage" and results in splitting of that hexose into two 3-carbon molecules. One of those 3-carbon molecules is recycled back through the RuMP pathway and the other 3-carbon fragment is utilized for cell growth.

In methanotrophs and methylotrophs the RuMP pathway may occur as one of three variants. However, only two of these variants are commonly found: the FBP/TA (fructose bisphosphotase/transaldolase) pathway or the KDPG/TA (keto deoxy phosphogluconate/transaldolase) pathway (Dijkhuizen, L., and Devries, G. E., "The Physiology and biochemistry of aerobic methanol-utilizing gram negative and gram positive bacteria". In: *Methane and Methanol Utilizers*; Colin Murrell and Howard Dalton, Eds.; Plenum: NY, 1992).

*Methylomonas* sp. 16a is unique in the way it handles the "cleavage" steps where genes were found that carry out this conversion via fructose bisphosphate as a key intermediate. The genes for fructose bisphosphate aldolase and transaldolase were found clustered together on one piece of DNA. Secondly, the genes for the other variant involving the keto deoxy phosphogluconate intermediate were also found clustered together. Available literature teaches that these organisms (obligate methylotrophs and methanotrophs) rely solely on the KDPG pathway and that the FBP-dependent fixation pathway is utilized by facultative methylotrophs (Dijkhuizen et al., supra). Therefore the latter observation is expected, whereas the former is not. The finding of the FBP genes in an obligate methane-utilizing bacterium is both surprising and suggestive of utility. The FBP pathway is energetically favorable to the host microorganism due to the fact that more energy (ATP) is utilized than is utilized in the KDPG pathway. Thus, organisms that utilize the FBP pathway may have an energetic advantage and growth advantage over those that utilize the KDPG pathway. This advantage may also be useful for energy-requiring production pathways in the strain. By using this pathway, a methane-utilizing bacterium may have an advantage over other methane-utilizing organisms as production platforms for either single cell protein or for any other product derived from the flow of carbon through the RuMP pathway (e.g., carotenoids).

Accordingly, the present invention provides a method for the production of a carotenoid compound in a high growth, energetically favorable *Methylomonas* strain which:
  (a) grows on a C1 carbon substrate selected from the group consisting of methane and methanol; and
  (b) comprises a functional Embden-Meyerhof carbon pathway, said pathway comprising a gene encoding a pyrophosphate-dependent phosphofructokinase enzyme.

Transformation of C1 Metabolizing Bacteria

Techniques for the transformation of C1 metabolizing bacteria are not well developed, although general methodology that is utilized for other bacteria, which is well known to those of skill in the art, may be applied. Electroporation has been used successfully for the transformation of: *Methylobacterium extorquens* AM1 (Toyama, H., et al., *FEMS Microbiol. Lett.* 166:1–7 (1998)), *Methylophilus methylotrophus* AS1 (Kim, C. S., and Wood, T. K., *Appl. Microbiol. Biotechnol.* 48: 105–108 (1997)), and *Methylobacillus* sp. strain 12S (Yoshida, T., et al., *Biotechnol. Lett.*, 23: 787–791 (2001)). Extrapolation of specific electroporation parameters from one specific C1 metabolizing utilizing organism to another may be difficult, however, as is well to known to those of skill in the art.

Bacterial conjugation, relying on the direct contact of donor and recipient cells, is frequently more readily amenable for the transfer of genes into C1 metabolizing bacteria. Simplistically, this bacterial conjugation process involves mixing together "donor" and "recipient" cells in close contact with one another. Conjugation occurs by formation of cytoplasmic connections between donor and recipient bacteria, with direct transfer of newly synthesized donor DNA into the recipient cells. As is well known in the art, the recipient in a conjugation is defined as any cell that can accept DNA through horizontal transfer from a donor bacterium. The donor in conjugative transfer is a bacterium that contains a conjugative plasmid, conjugative transposon, or mobilizable plasmid. The physical transfer of the donor plasmid can occur in one of two fashions, as described below:

1. In some cases, only a donor and recipient are required for conjugation. This occurs when the plasmid to be transferred is a self-transmissible plasmid that is both conjugative and mobilizable (i.e., carrying both tra-genes and genes encoding the Mob proteins). In general, the process involves the following steps: 1.) Double-strand plasmid DNA is nicked at a specific site in oriT; 2.) A single-strand DNA is released to the recipient through a pore or pilus structure; 3.) A DNA relaxase enzyme cleaves the double-strand DNA at oriT and binds to a release 5' end (forming a relaxosome as the intermediate structure); and 4.) Subsequently, a complex of auxiliary proteins assemble at oriT to facilitate the process of DNA transfer.

2. Alternatively, a "triparental" conjugation is required for transfer of the donor plasmid to the recipient. In this type of conjugation, donor cells, recipient cells, and a "helper" plasmid participate. The donor cells carry a mobilizable plasmid or conjugative transposon. Mobilizable vectors contain an oriT, a gene encoding a nickase, and have genes encoding the Mob proteins; however, the Mob proteins alone are not sufficient to achieve the transfer of the genome. Thus, mobilizable plasmids are not able to promote their own transfer unless an appropriate conjugation system is provided by a helper plasmid (located within the donor or within a "helper" cell). The conjugative plasmid is needed for the formation of the mating pair and DNA transfer, since the plasmid encodes proteins for transfer (Tra) that are involved in the formation of the pore or pilus.

Examples of successful conjugations involving C1 metabolizing bacteria include the work of: Stolyar et al. (*Mikrobiologiya* 64(5): 686–691 (1995)); Motoyama et al. (*Appl. Micro. Biotech.* 42(1): 67–72 (1994)); Lloyd et al. (*Archives of Microbiology* 171(6): 364–370 (1999)); and Odom et al. (WO 02/18617).

In vitro Bio-Conversion of Carotenoids

Alternatively, it is possible to carry out the bioconversions of the present application in vitro. Where substrates for CrtE, CrtX, CrtY, CrtI, CrtB, and CrtZ are not synthesized endogenously by the host cell it will be possible to add the substrate exogenously. In this embodiment the suitable carotenoid substrate may be solubilized with mild detergent (e.g., DMSO) or mixed with phospholipid vesicles. To assist in transport into the cell, the host cell may optionally be permeabilized with a suitable solvent such as toluene. Methods for this type of in-vitro bio-conversion of carotenoid substrates has basis in the art (see for example: Hundle, B. S., et al., *FEBS*, 315:329–334 (1993); and Bramley, P. M., et al., *Phytochemistry*, 26:1935–1939 (1987)).

Industrial Production Using Recombinant Microorganisms

Where commercial production of the instant proteins are desired, a variety of culture methodologies may be applied. For example, large-scale production of a specific gene product over-expressed from a recombinant microbial host may be produced by both batch and continuous culture methodologies.

A classical batch culturing method is a closed system where the composition of the media is set at the beginning of the culture and not subject to artificial alterations during the culturing process. Thus, at the beginning of the culturing process the media is inoculated with the desired organism or organisms and growth or metabolic activity is permitted to occur while adding nothing to the system. Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of end product or intermediate in some systems. Stationary or post-exponential phase production can be obtained in other systems.

A variation on the standard batch system is the Fed-Batch system. Fed-Batch culture processes are also suitable in the present invention and comprise a typical batch system with the exception that the substrate is added in increments as the culture progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch culturing methods are common and well known in the art and examples may be found in Brock (supra) and Deshpande (supra).

Commercial production of the instant proteins may also be accomplished with a continuous culture. Continuous cultures are an open system where a defined culture media is added continuously to a bioreactor and an equal amount of conditioned media is removed simultaneously for processing. Continuous cultures generally maintain the cells at a constant high liquid phase density where cells are primarily in log phase growth. Alternatively continuous culture may be practiced with immobilized cells where carbon and nutrients are continuously added, and valuable products, by-products or waste products are continuously removed from the cell mass. Cell immobilization may be performed using a wide range of solid supports composed of natural and/or synthetic materials.

Continuous or semi-continuous culture allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the culture. Methods of modulating nutrients and growth factors for continuous culture processes, as well as techniques for maximizing the rate of product formation, are well known in the art of industrial microbiology and a variety of methods are detailed by Brock, supra.

Fermentation media in the present invention must contain suitable carbon substrates. Suitable substrates may include, but are not limited to: monosaccharides (e.g., glucose and fructose), disaccharides (e.g., lactose or sucrose), polysaccharides (e.g., starch or cellulose or mixtures thereof) and unpurified mixtures from renewable feedstocks (e.g., cheese whey permeate, cornsteep liquor, sugar beet molasses, and barley malt). Additionally, the carbon substrate may also be one-carbon substrates such as carbon dioxide, methane or methanol for which metabolic conversion into key biochemical intermediates has been demonstrated. In addition to one and two carbon substrates, methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., *Microb. Growth C1 Compd.*, [Int. Symp.], 7$^{th}$ (1993), 415–32. Murrell, J. Collin and Kelly, Don P, eds. Intercept: Andover, UK). Similarly, various species of *Candida* will metabolize alanine or oleic acid (Sulter et al., *Arch. Microbiol.* 153:485–489 (1990)). Hence it is contemplated that the source of carbon utilized in the present invention may encompass a wide variety of carbon-containing substrates and will only be limited by the choice of organism.

Recombinant Production in Plants

Plants and algae are also known to produce carotenoid compounds. The crtE, crtX, crtY, crtI, crtB and crtZ nucleic acid fragments of the instant invention may be used to create transgenic plants having the ability to express the microbial protein(s). Preferred plant hosts will be any variety that will support a high production level of the instant proteins. Suitable green plants will include, but are not limited to: soybean, rapeseed (*Brassica napus, B. campestris*), sunflower (*Helianthus annus*), cotton (*Gossypium hirsutum*), corn, tobacco (*Nicotiana tabacum*), alfalfa (*Medicago* sativa), wheat (*Triticum* sp.), barley (*Hordeum vulgare*), oats (*Avena sativa*, L), sorghum (*Sorghum bicolor*), rice (*Oryza sativa*), *Arabidopsis*, cruciferous vegetables (broccoli, cauliflower, cabbage, parsnips, etc.), melons, carrots, celery, parsley, tomatoes, potatoes, strawberries, peanuts, grapes, grass seed crops, sugar beets, sugar cane, beans, peas, rye, flax, hardwood trees, softwood trees, and forage grasses. Algal species include, but are not limited to, commercially significant hosts such as *Spirulina, Haemotacoccus*, and *Dunalliela*.

Over-expression of the carotenoid compounds may be accomplished by first constructing chimeric genes of the present invention in which the coding region(s) are operably linked to promoters capable of directing expression of a gene(s) in the desired tissues at the desired stage of development. For reasons of convenience, the chimeric genes may comprise promoter sequences and translation leader sequences derived from the same genes. 3' Non-coding sequences encoding transcription termination signals must also be provided. The instant chimeric genes may also comprise one or more introns in order to facilitate gene expression.

Any combination of any promoter and any terminator capable of inducing expression of a coding region may be used in the chimeric genetic sequence. Some suitable examples of promoters and terminators include those from nopaline synthase (nos), octopine synthase (ocs) and cauliflower mosaic virus (CaMV) genes. One type of efficient plant promoter that may be used is a high-level plant promoter. Such promoters, in operable linkage with the genetic sequences of the present invention, should be capable of promoting expression of the present gene product. High-level plant promoters that may be used in this invention include, for example: 1.) the promoter of the small subunit (ss) of the ribulose-1,5-bisphosphate carboxylase from soybean (Berry-Lowe et al., *J. Molecular and App. Gen.,* 1:483–498 (1982)); and 2.) the promoter of the chlorophyll a/b binding protein. These two promoters are known to be light-induced in plant cells (see, for example, *Genetic Engineering of Plants, an Agricultural Perspective*, A. Cashmore, Ed. Plenum: NY (1983), pp 29–38; Coruzzi, G. et al., *J. Biol. Chem.,* 258:1399 (1983); and Dunsmuir, P. et al., *J. Mol. Appl. Genet.,* 2:285 (1983)).

Plasmid vectors comprising the instant chimeric genes can then be constructed. The choice of plasmid vector depends upon the method that will be used to transform host plants. The skilled artisan is well aware of the genetic elements that must be present on the plasmid vector in order to successfully transform, select and propagate host cells containing the chimeric gene(s). The skilled artisan will also recognize that different independent transformation events will result in different levels and patterns of expression (Jones et al., *EMBO J.* 4:2411–2418 (1985); De Almeida et al., *Mol. Gen. Genetics* 218:78–86 (1989)), and thus multiple events must be screened in order to obtain lines displaying the desired expression level and pattern. Such screening may be accomplished by Southern analysis of DNA blots (Southern, *J. Mol. Biol.* 98:503 (1975)), Northern analysis of mRNA expression (Kroczek, *J. Chromatogr. Biomed. Appl.,* 618 (1–2):133–145 (1993)), Western analysis of protein expression, or phenotypic analysis.

For some applications it will be useful to direct the instant proteins to different cellular compartments. It is thus envisioned that the chimeric genes described above may be further supplemented by altering the coding sequences to encode enzymes with appropriate intracellular targeting sequences added and/or with targeting sequences that are already present removed, such as: 1.) transit sequences (Keegstra, K., *Cell* 56:247–253 (1989)); 2.) signal sequences; or 3.) sequences encoding endoplasmic reticulum localization (Chrispeels, J. J., *Ann. Rev. Plant Phys. Plant Mol. Biol.* 42:21–53 (1991)) or nuclear localization signals (Raikhel, N., *Plant Phys.* 100:1627–1632 (1992)). While the references cited give examples of each of these, the list is not exhaustive and more targeting signals of utility may be discovered in the future that are useful in the invention.

Protein Engineering

It is contemplated that the present crtE, crtX, crtY, crtI, crtB, and crtZ nucleotides may be used to produce gene products having enhanced or altered activity. Various methods are known for mutating a native gene sequence to produce a gene product with altered or enhanced activity including, but not limited to: 1.) error prone PCR (Melnikov et al., *Nucleic Acids Research,* 27(4):1056–1062 (Feb. 15, 1999)); 2.) site directed mutagenesis (Coombs et al., *Proteins* (1998), pp 259–311, 1 plate. Angeletti, Ruth Hogue, Ed., Academic: San Diego, Calif.); and 3.) "gene shuffling" (U.S. Pat. No. 5,605,793; U.S. Pat. No. 5,811,238; U.S. Pat. No. 5,830,721; and U.S. Pat. No. 5,837,458, incorporated herein by reference).

The method of gene shuffling is particularly attractive due to its facile implementation, and high rate of mutagenesis and ease of screening. The process of gene shuffling involves the restriction endonuclease cleavage of a gene of interest into fragments of specific size in the presence of additional populations of DNA fragments having regions of both similarity or difference to the gene of interest. This pool of fragments will then be denatured and reannealed to create a mutated gene. The mutated gene is then screened for altered activity.

The instant microbial sequences of the present invention may be mutated and screened for altered or enhanced activity by this method. The sequences should be double-stranded and can be of various lengths ranging from 50 bp to 10 kB. The sequences may be randomly digested into fragments ranging from about 10 bp to 1000 bp, using restriction endonucleases well known in the art (Maniatis, supra). In addition to the instant microbial sequences, populations of fragments that are hybridizable to all or portions of the microbial sequence may be added. Similarly, a population of fragments which are not hybridizable to the instant sequence may also be added. Typically these additional fragment populations are added in about a 10 to 20 fold excess by weight as compared to the total nucleic acid. Generally, if this process is followed, the number of different specific nucleic acid fragments in the mixture will be about 100 to about 1000. The mixed population of random nucleic acid fragments are denatured to form single-stranded nucleic acid fragments and then reannealed. Only those single-stranded nucleic acid fragments having regions of homology with other single-stranded nucleic acid fragments will reanneal. The random nucleic acid fragments may be denatured by heating. One skilled in the art could determine the conditions necessary to completely denature the double-stranded nucleic acid. Preferably the temperature is from about 80° C. to 100° C. The nucleic acid fragments may be reannealed by cooling. Preferably the temperature is from about 20° C. to 75° C. Renaturation can be accelerated by the addition of polyethylene glycol ("PEG") or salt. A suitable salt concentration may range from 0 mM to 200 mM. The annealed nucleic acid fragments are then incubated in the presence of a nucleic acid polymerase and dNTPs (i.e., dATP, dCTP, dGTP and dTTP). The nucleic acid polymerase may be the Klenow fragment, the Taq polymerase or any other DNA polymerase known in the art. The polymerase may be added to the random nucleic acid fragments prior to annealing, simultaneously with annealing or after annealing. The cycle of denaturation, renaturation and incubation in the presence of polymerase is repeated for a desired number of times. Preferably the cycle is repeated from about 2 to 50 times, more preferably the sequence is repeated from 10 to 40 times. The resulting nucleic acid is a larger double-stranded polynucleotide ranging from about 50 bp to about 100 kB and may be screened for expression and altered activity by standard cloning and expression protocols (Maniatis, supra).

Furthermore, a hybrid protein can be assembled by fusion of functional domains using the gene shuffling (exon shuffling) method (Nixon et al., *Proc. Natl. Acad. Sci.*, 94:1069–1073 (1997)). The functional domain of the instant gene can be combined with the functional domain of other genes to create novel enzymes with desired catalytic function. A hybrid enzyme may be constructed using PCR overlap extension methods and cloned into various expression vectors using the techniques well known to those skilled in art.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by: Maniatis (supra), Silhavy (supra), and Ausubel et al. (supra).

Materials and methods suitable for the maintenance and growth of bacterial cultures are well known in the art. Techniques suitable for use in the following examples may be found as set out in: *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, Eds), American Society for Microbiology: Washington, D.C. (1994)); or in Brock (supra). All reagents, restriction enzymes and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

Sequence data was generated on an ABI Automatic sequencer using dye terminator technology (U.S. Pat. No. 5,366,860; EP 272,007) using a combination of vector and insert-specific primers. Sequence editing and assembly was performed in Sequencher™ version 4.0.5 (Gene Codes Corp., Ann Arbor, Mich.). All sequences represent coverage at least two times in both directions. Manipulations of genetic sequences were accomplished using Vector NTI programs (Informax, Inc., Bethesda, Md.). Pairwise comparisons were performed using the default values in Vector NTI. BLAST analysis was performed using the default values set in the National Center for Biotechnology Information (NCBI) website.

The meaning of abbreviations is as follows: "sec" means second(s), "min" means minute(s), "h" means hour(s), "d" means day(s), "µL" means microliter(s), "mL" means milliliter(s), "L" means liter(s), "µM" means micromolar, "mM" means millimolar, "M" means molar, "mmol" means millimole(s), "µmol" mean micromole(s), "g" means gram(s), "µg" means microgram(s), "ng" means nanogram(s), "U" means unit(s), "bp" means base pair(s), and "kB" means kilobase(s).

Example 1

Isolation of a Carotenoid-Producing Strain DC260

The present Example describes the isolation and identification of a yellow-pigmented bacterium designated as strain DC260, which belongs to the family Enterobacteriaceae. Analysis of the native carotenoids produced in this organism confirms production of zeaxanthin, in addition to various zeaxanthin precursors and zeaxanthin derivatives.

Strain isolation and 16S rRNA typing: To isolate novel carotenoid producing bacterial strains, pigmented microbes were isolated from a collection of environmental samples. The surface of a brick on a west-facing wall in a suburb of Wilmington, Delaware was washed with 10 mL of tap water and the water was collected. A 10 µL loopful of the water was streaked onto Luria-Broth (LB) plates and the plates were incubated at 30° C. Pigmented bacteria with diverse colony appearances were picked and streaked twice to homogeneity on LB plates and incubated at 30° C. From these colonies, one which formed pale yellow smooth translucent colonies was designated as "strain DC260".

Strain DC260 was typed by 16S rRNA gene sequencing. Specifically, the 16S rRNA gene of the strain was amplified by PCR using primers HK12 (SEQ ID NO:13) and JCR14 (SEQ ID NO:14). The amplified 16S rRNA genes were purified using a QIAquick PCR Purification Kit according to the manufacturer's instructions (Qiagen) and sequenced on an automated ABI sequencer. The sequencing reactions were initiated with primers HK12, JCR14, and JCR15 (SEQ ID NO:15). The assembled 1327 bp 16S rRNA gene sequence (SEQ ID NO:16) was used as the query sequence for a BLASTN search (Altschul et al., *Nucleic Acids Res.* 25:3389–3402(1997)) against GenBank®. The 16S rDNA sequencing indicated that this strain belongs to the Enterobacteriaceae family sharing 98% sequence identity with the 16S rDNA sequence of strains typed as *Leclercia adecarboxylata* and *Enterobacter intermedius*, two BSL1 organisms.

Carotenoid analysis of DC260: The yellow pigment in DC260 was extracted and analyzed by HPLC. The strain was grown in 100 mL LB at 30° C. for 18 h. The cells were harvested by centrifugation at 4000 g for 15 min. The cell pellet was extracted with 5 mL acetone+5 mL methanol. The solvent was dried under nitrogen and the carotenoids were resuspended in 0.5 mL acetone+0.5 mL methanol for HPLC analysis. The extraction was filtered with an Acrodisc® CR25 mm syringe filter (Pall Corporation, Ann Arbor, Mich.) and was analyzed using an Agilent Series 1100 LC/MSD SI (Agilent, Foster City, Calif.).

Sample (20 µL) was loaded onto a 150 mm×4.6 mm ZORBAX C18 (3.5 µm particles) column (Agilent Technologies, Inc.). The column temperature was kept at 40° C. The flow rate was 1 mL/min, while the solvent running program used was:
- 0–2 min: 95% buffer A and 5% buffer B;
- 2–10 min: linear gradient from 95% buffer A and 5% buffer B to 60% buffer A and 40% buffer B;
- 10–12 min: linear gradient from 60% buffer A and 40% buffer B to 50% buffer A and 50% buffer B;
- 12–18 min: 50% buffer A and 50% buffer B; and,
- 18–20 min: 95% buffer A and 5% buffer B.

Buffer A was 95% acetonitrile and 5% dH$_2$O; buffer B was 100% tetrahydrofuran.

HPLC analysis (FIG. 3) indicated that strain DC260 produced zeaxanthin (5.76 min peak) and β-cryptoxanthin (9.78 min peak) by comparison with the authentic standards of zeaxanthin and β-cryptoxanthin purchased from Carote-Nature (Lupsingen, Switzerland). MS analysis confirmed that the molecular weight of the zeaxanthin peak was 569 and that of the β-cryptoxanthin peak was 553. The other peaks that eluted earlier than zeaxanthin are likely zeaxanthin derivatives (e.g., zeaxanthin monoglucoside and diglucoside) as suggested by LC/MS.

Example 2

Identification of Pigmented Cosmid Clones of Strain DC260

Example 2 describes the construction of an *E. coli* cosmid clone capable of expressing an ~40 kB fragment of genomic DNA from strain DC260. This transformant produced zeaxanthin, in addition to various zeaxanthin precursors and zeaxanthin derivatives.

Chromosomal DNA preparation: Strain DC260 was grown in 25 mL LB medium at 30° C. overnight with aeration. Bacterial cells were centrifuged at 4,000 g for 10 min. The cell pellet was gently resuspended in 5 mL of 50 mM Tris-10 mM EDTA (pH 8) and lysozyme was added to a final concentration of 2 mg/mL. The suspension was incubated at 37° C. for 1 h. Sodium dodecyl sulfate was then added to a final concentration of 1% and proteinase K was added at 100 μg/mL. The suspension was incubated at 55° C. for 2 h. The suspension became clear and the clear lysate was extracted twice with an equal volume of phenol:chloroform:isoamyl alcohol (25:24:1) and once with chloroform:isoamyl alcohol (24:1). After centrifuging at 4,000 rpm for 20 min, the aqueous phase was carefully removed and transferred to a new tube. Two volumes of ethanol were added and the DNA was gently spooled with a sealed glass pasteur pipette. The DNA was dipped into a tube containing 70% ethanol. After air drying, the DNA was resuspended in 400 μL of TE (10 mM Tris-1 mM EDTA, pH 8) with RNaseA (100 μg/mL) and stored at 4° C. The concentration and purity of DNA was determined spectrophotometrically by OD$_{260}$/OD$_{280}$.

Cosmid library construction: A cosmid library of DC260 was constructed using the pWEB cosmid cloning kit from Epicentre Technologies (Madison, Wis.) following the manufacturer's instructions. Genomic DNA was sheared by passing it through a syringe needle. The sheared DNA was end-repaired and size-selected on low-melting-point agarose by comparison with a 40-kB standard. DNA fragments approximately 40 kB in size were purified and ligated into the blunt-ended cloning-ready pWEB cosmid vector. The library was packaged using ultra-high efficiency MaxPlax Lambda Packaging Extracts, and plated on the EPI100 *E. coli* cells. Two yellow colonies were identified from the cosmid library clones. Since cosmid DNA from the two clones had similar restriction digestion patterns, further analysis was performed on a single clone.

Carotenoid analysis of the yellow cosmid clone: The carotenoids in *E. coli* EPI100 containing cosmid pWEB-260 were analyzed by LC-MS, as described in EXAMPLE 1. The HPLC result is shown in FIG. 4. The 5.74 min peak was identified as zeaxanthin, based on its UV spectrum, molecular weight and comparison with the authentic standard. No β-carotene or β-cryptoxanthin intermediates accumulated. Other peaks that eluted earlier than zeaxanthin are most likely zeaxanthin derivatives (e.g., zeaxanthin monoglucoside and diglucoside).

Example 3

Identification of Carotenoid Biosynthesis Genes

This Example describes the identification of strain DC260 crtE, crtX, crtY, crtI, crtB, and crtZ genes in cosmid pWEB-260, and provides a comparison of the relatedness of these genes with respect to other known *Panteoa* crt genes.

HPLC analysis suggested that cosmid pWEB-260 should contain genes for synthesis of zeaxanthin and its derivatives. To sequence the carotenoid synthesis genes, cosmid DNA pWEB-260 was subjected to in vitro transposition using the EZ::TN <TET-1> kit from Epicentre (Madison, Wis.) following the manufacturer's instructions. Two hundred tetracycline resistant transposon insertions were sequenced from the end of the transposon using the TET-1 FP-1 Forward primer (SEQ ID:17). Sequence assembly was performed with the Sequencher program (Gene Codes Corp., Ann Arbor, Mich.). A 6999 bp contig (SEQ ID:18) containing carotenoid synthesis genes from DC260 was assembled (FIG. 5).

Genes encoding crtE, crtX, crtY, crtI, crtB, and crtZ were identified by conducting BLAST (Basic Local Alignment Search Tool; Altschul, S. F., et al., supra) searches for similarity to sequences contained in the BLAST "nr" database (comprising all non-redundant GenBank® CDS translations, sequences derived from the 3-dimensional structure Brookhaven Protein Data Bank, the SWISS-PROT protein sequence database, EMBL, and DDBJ databases). The sequence was analyzed for similarity to all publicly available DNA sequences contained in the "nr" database using the BLASTN algorithm provided by the National Center for Biotechnology Information (NCBI). The DNA sequence was translated in all reading frames and compared for similarity to all publicly available protein sequences contained in the "nr" database using the BLASTX algorithm (Gish, W. and States, D. J., *Nature Genetics* 3:266–272 (1993)) provided by the NCBI.

All comparisons were done using either the BLASTNnr or BLASTXnr algorithm. The results of the BLAST comparisons are given in Table 2, which summarizes the sequences to which each gene has the most similarity. Table 2 displays data based on the BLASTXnr algorithm with values reported in expect values. The Expect value estimates the statistical significance of the match, specifying the number of matches, with a given score, that are expected in a search of a database of this size absolutely by chance.

The nucleotide and amino acid sequences of strain DC260 were also compared with those from various *Pantoea* strains. Table 3 summarizes the identity for the pairwise comparisons.

TABLE 2

Top BLAST Hits for the Carotenoid Synthesis Genes of Strain DC260

| ORF Name | Gene Name | Similarity Identified | SEQ ID base | SEQ ID Peptide | % Identity a | % Similarity b | E-value c | Citation |
|---|---|---|---|---|---|---|---|---|
| 1 | crtE | Geranylgeranyl pryophosphate synthetase (or synthetase, or farnesyltranstransferase) EC 2.5.1.29 gi|18143445|dbj|BAB79600.1| crtE [Pantoea agglomerans pv. milletiae] | 1 | 2 | 54 | 66 | 6e–74 | Kamiunten, H. and Hirata, R. (2001), Unpublished |
| 2 | crtX | Zeaxanthin glucosyl transferase EC 2.4.1.— gi|27228291|gb|AAN85597.1| Zeaxanthin Glucosyl Transferase [Pantoea stewartii] | 3 | 4 | 52 | 66 | e–119 | deSouza, M. L., et al. (2002), Unpublished |
| 3 | crtY | Lycopene cyclase gi|216684|dbj|BAA14126.1| crtY [Pantoea ananatis] | 5 | 6 | 53 | 64 | e–111 | Misawa, N., et al., J. Bacteriol. 172 (12): 6704–6712 (1990) |
| 4 | crtI | Phytoene desaturase EC 1.3.—.— gi|18143448|dbj|BAB79603.1| crtI [Pantoea agglomerans pv. milletiae] | 7 | 8 | 77 | 84 | 0.0 | Kamiunten, H. and Hirata, R. (2001) unpublished |
| 5 | crtB | Phytoene synthaseEC2.5.1.— gi|22474503|dbj|BAA14128.2| crtB [Pantoea ananatis] | 9 | 10 | 60 | 69 | e–103 | Misawa, N., et al., J. Bacteriol. 172 (12): 6704–6712 (1990) |
| 6 | crtZ | Beta-carotene hydroxylase gi|27228295|gb|AAN85601.1| Beta-Carotene Hydroxylase [Pantoea stewartii] | 11 | 12 | 66 | 73 | 5e–66 | deSouza, M. L., et al. (2002), Unpublished |

[a]% Identity is defined as percentage of amino acids that are identical between the two proteins.
[b]% Similarity is defined as percentage of amino acids that are identical or conserved between the two proteins.
[c]Expect value. The Expect value estimates the statistical significance of the match, specifying the number of matches, with a given score, that are expected in a search of a database of this size absolutely by chance.

TABLE 3

Pairwise Comparison of the Carotenoid Biosynthesis Genes from Strain DC260 with Those from Various *Pantoea* Strains

| Source/gene | *Pantoea ananatis*[a] | | *Pantoea agglomerans*[b] | | *Pantoea stewartii*[c] | |
|---|---|---|---|---|---|---|
| | DNA | Amino acid | DNA | Amino acid | DNA | Amino acid |
| DC260, crtE | 63% | 58% | 57% | 51% | 63% | 58% |
| DC260, crtX | 58% | 52% | 57% | 49% | 60% | 54% |
| DC260, crtY | 59% | 57% | 60% | 57% | 60% | 58% |
| DC260, crtI | 72% | 81% | 71% | 76% | 71% | 80% |
| DC260, crtB | 66% | 66% | 64% | 64% | 62% | 64% |
| DC260, crtZ | 72% | 76% | 67% | 65% | 73% | 76% |

[a]*Pantoea ananatis*, GenBank ® Accession Number D90087
[b]*Pantoea agglomerans*, GenBank ® Accession Number M87280
[c]*Pantoea stewartii*, GenBank ® Accession Number AY166713

Example 4

Expression of the crtEXYIB Gene Cluster of DC260 in *Methylomonas* sp. 16a

The following Example describes the introduction of the crt gene cluster comprising the crtEXYIB genes from DC260 (Example 3) into *Methylomonas* 16a (ATCC PTA 2402) to enable the synthesis of desirable 40-carbon carotenoids, such as β-carotene.

First, primers pWEB260F: 5'-GAATTCACCAACCATG-GATAGCCATTATGAC-3' (SEQ ID NO:19) and pWEB260R: 5'-GAATTCAACGAGGACGCTGCCA-CAGA-3' (SEQ ID NO:20) were used to amplify a fragment from DC260 containing the crtEXYIB genes by PCR. Cosmid DNA pWEB-260 was used as the template with Pfu Turbo polymerase (Stratagene, La Jolla, Calif.), and the following thermocycler conditions: 92° C. (5 min); 94° C. (1 min), 60° C. (1 min), 72° C. (9 min) for 25 cycles; and 72° C. (10 min). A single product of approximately 5.8 kB was observed following gel electrophoresis. Taq polymerase (Perkin Elmer) was used in a ten minute 72° C. reaction to add additional 3' adenosine nucleotides to the fragment for TOPO cloning into pTrcHis2-TOPO (Invitrogen, Carlsbad, Calif.). Following transformation to *E. coli* TOP10 cells, several colonies appeared yellow in color, indicating that they were producing a carotenoid compound. The gene cluster was then subcloned into the broad host range vector pBHR1 (MoBiTec, LLC, Marco Island, Fla.), and electroporated into *E. coli* 10G cells (Lucigen, Middletown, Wis.). The transformants containing the resulting plasmid pDCQ329 were selected on LB medium containing 50 µg/mL kanamycin.

Plasmid pDCQ329 was transferred into *Methylomonas* 16a by tri-parental conjugal mating. The *E. coli* helper strain containing pRK2013 (ATCC No. 37159) and the *E. coli* 10G donor strain containing pDCQ329 were growing overnight in LB medium containing kanamycin (50 µg/mL), washed three times in LB, and resuspended in a volume of LB representing approximately a 60-fold concentration of the original culture volume.

The *Methylomonas* 16a MWM1000 (Δald/CrtN1) strain contained a single crossover knockout of the ald/crtN1 genes, which disrupted the synthesis of the native $C_{30}$ carotenoids (U.S. Pat. Ser. No. 60/527,083). This (Δald/CrtN1) strain was growing as the recipient using the general conditions described in WO 02/18617. Briefly, *Methylomonas* 16a MWM1000 strain was growing in serum stoppered Wheaton bottles (Wheaton Scientific, Wheaton Ill.) using a gas/liquid ratio of at least 8:1 (i.e., 20 mL of Nitrate liquid "BTZ-3" media in 160 mL total volume) at 30° C. with constant shaking.

Nitrate liquid medium, also referred to herein as "defined medium" or "BTZ-3" medium was comprised of various salts mixed with Solution 1 as indicated below (Tables 4 and 5) or where specified the nitrate was replaced with 15 mM ammonium chloride. Solution 1 provides the composition for 100-fold concentrated stock solution of trace minerals.

TABLE 4

Solution 1*

|  | MW | Conc. (mM) | g per L |
|---|---|---|---|
| Nitriloacetic acid | 191.1 | 66.9 | 12.8 |
| CuCl$_2$ × 2H$_2$O | 170.48 | 0.15 | 0.0254 |
| FeCl$_2$ × 4H$_2$O | 198.81 | 1.5 | 0.3 |
| MnCl$_2$ × 4H$_2$O | 197.91 | 0.5 | 0.1 |
| CoCl$_2$ × 6H$_2$O | 237.9 | 1.31 | 0.312 |
| ZnCl$_2$ | 136.29 | 0.73 | 0.1 |
| H$_3$BO$_3$ | 61.83 | 0.16 | 0.01 |
| Na$_2$MoO$_4$ × 2H$_2$O | 241.95 | 0.04 | 0.01 |
| NiCl$_2$ × 6H$_2$O | 237.7 | 0.77 | 0.184 |

*Mix the gram amounts designated above in 900 mL of H$_2$O, adjust to pH = 7, and add H$_2$O to an end volume of 1 L. Keep refrigerated.

TABLE 5

Nitrate liquid medium (BTZ-3)**

|  | MW | Conc. (mM) | g per L |
|---|---|---|---|
| NaNO$_3$ | 84.99 | 10 | 0.85 |
| KH$_2$PO$_4$ | 136.09 | 3.67 | 0.5 |
| Na$_2$SO$_4$ | 142.04 | 3.52 | 0.5 |
| MgCl$_2$ × 6H$_2$O | 203.3 | 0.98 | 0.2 |
| CaCl$_2$ × 2H$_2$O | 147.02 | 0.68 | 0.1 |
| 1 M HEPES (pH 7) | 238.3 |  | 50 mL |
| Solution 1 |  |  | 10 mL |

**Dissolve in 900 mL H$_2$O. Adjust to pH = 7, and add H$_2$O to give 1 L. For agar plates: Add 15 g of agarose in 1 L of medium, autoclave, let cool down to 50° C., mix, and pour plates.

The standard gas phase for cultivation contains 25% methane in air. The MWM1000 recipient was cultured under these conditions for 48 h in BTZ-3 medium, washed three times in BTZ-3, and resuspended in a volume of BTZ-3 representing a 150-fold concentration of the original culture volume.

The donor, helper, and recipient cell pastes were then combined in ratios of 1:1:2, respectively, on the surface of BTZ-3 agar plates containing 0.5% (w/v) yeast extract. Plates were maintained at 30° C. in 25% methane for 16–72 hours to allow conjugation to occur, after which the cell pastes were collected and resuspended in BTZ-3. Dilutions were plated on BTZ-3 agar containing kanamycin (50 μg/mL) and incubated at 30° C. in 25% methane for up to 1 week. Yellow transconjugants were streaked onto BTZ-3 agar with kanamycin (50 μg/mL).

For analysis of carotenoid composition, transconjugants were cultured in 25 mL BTZ-3 containing kanamycin (50 μg/mL) and incubated at 30° C. in 25% methane as the sole carbon source for 3–4 days. The cells were harvested by centrifugation and frozen at −20° C. After thawing, the pellets were extracted and carotenoid content was analyzed by HPLC, as described in Example 1.

HPLC analysis of extracts from *Methylomonas* 16a containing pDCQ329 showed almost exclusive production of β-carotene (FIG. 6). The retention time, UV spectrum and the molecular weight of the 14 min peak match those of the authentic β-carotene standard (Sigma, St. Louis, Mo.). This confirmed the synthesis of C$_{40}$ carotenoids in this methanotrophic host using the crtEXYIB gene cluster from DC260.

What is claimed is:

1. An isolated nucleic acid molecule as set forth in SEQ ID NO:18, wherein the isolated nucleic acid molecule encodes all of the polypeptides crtE, crtX, crtY, crtI, crtB and crtZ.

* * * * *